(12) United States Patent
Holmes, Jr. et al.

(10) Patent No.: US 12,295,651 B2
(45) Date of Patent: May 13, 2025

(54) DEVICES AND METHODS FOR ABLATION OF TISSUE

(71) Applicant: Mayo Foundation for Medical Education and Research, Rochester, MN (US)

(72) Inventors: David R. Holmes, Jr., Rochester, MN (US); Samuel J. Asirvatham, Rochester, MN (US); Christopher V. DeSimone, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 301 days.

(21) Appl. No.: 17/867,505

(22) Filed: Jul. 18, 2022

(65) Prior Publication Data
US 2022/0346870 A1 Nov. 3, 2022

Related U.S. Application Data

(62) Division of application No. 15/771,593, filed as application No. PCT/US2016/058629 on Oct. 25, 2016, now abandoned.
(Continued)

(51) Int. Cl.
*A61B 18/12* (2006.01)
*A61B 18/14* (2006.01)
(Continued)

(52) U.S. Cl.
CPC ..... *A61B 18/1492* (2013.01); *A61M 25/1011* (2013.01); *A61B 2018/0022* (2013.01);
(Continued)

(58) Field of Classification Search
CPC ...... A61B 18/1492; A61B 2018/00285; A61B 2018/00375; A61B 2018/00404;
(Continued)

(56) References Cited

U.S. PATENT DOCUMENTS

| 5,366,443 A | 11/1994 | Eggers et al. |
| 5,868,736 A | 2/1999 | Swanson et al. |

(Continued)

FOREIGN PATENT DOCUMENTS

| NO | 871205 L | 9/1988 |
| WO | WO 2000/042934 A1 | 7/2000 |

(Continued)

OTHER PUBLICATIONS

Extended European Search Report in European Application No. 16860607.7 dated Apr. 1, 2019, 48 pages.
(Continued)

*Primary Examiner* — Daniel W Fowler
(74) *Attorney, Agent, or Firm* — Fish & Richardson P.C.

(57) ABSTRACT

Devices and methods for the treatment of heart conditions, hypertension, and other medical disorders are described. For example, this document describes devices and methods for treating atrial fibrillation by performing thoracic vein ablation procedures, including pulmonary vein myocardium ablation. In some embodiments, the ablation is performed in coordination with the delivery a pharmacological agent that can abate the formation of tissue stenosis or neointimal hyperplasia caused by the ablation. Additionally, in some embodiments, particulate matter, such as thrombus or crystalline drug compounds, created during the ablation is captured and removed from the patient using devices and methods provided herein. Further, devices and methods for non-thermal methods of causing cell death, such as tissue suction and tissue stretching, are also described.

18 Claims, 12 Drawing Sheets

Related U.S. Application Data

(60) Provisional application No. 62/247,048, filed on Oct. 27, 2015.

(51) Int. Cl.
*A61M 25/10* (2013.01)
*A61B 18/00* (2006.01)

(52) U.S. Cl.
CPC ............ *A61B 2018/00285* (2013.01); *A61B 2018/00375* (2013.01); *A61B 2018/00404* (2013.01); *A61B 2018/00434* (2013.01); *A61B 2018/00511* (2013.01); *A61B 2018/00577* (2013.01); *A61B 2018/1266* (2013.01); *A61B 2218/002* (2013.01); *A61B 2218/007* (2013.01); *A61M 2025/105* (2013.01); *A61M 2205/054* (2013.01)

(58) Field of Classification Search
CPC .......... A61B 2018/00434; A61B 2018/00511; A61B 2018/00577; A61B 2018/1266
See application file for complete search history.

(56) References Cited

U.S. PATENT DOCUMENTS

| | | | |
|---|---|---|---|
| 5,938,660 A * | 8/1999 | Swartz | A61M 25/1011 606/45 |
| 5,989,281 A | 11/1999 | Barbut et al. | |
| 6,012,457 A | 1/2000 | Lesh | |
| 6,235,044 B1 | 5/2001 | Root et al. | |
| 6,305,378 B1 | 10/2001 | Lesh | |
| 6,315,778 B1 | 11/2001 | Gambale et al. | |
| 6,425,877 B1 | 7/2002 | Edwards | |
| 6,491,710 B2 | 12/2002 | Satake | |
| 6,692,490 B1 | 2/2004 | Edwards | |
| 6,925,327 B2 | 5/2005 | Altman | |
| 7,192,438 B2 | 3/2007 | Margolis | |
| 8,043,351 B2 | 10/2011 | Yon et al. | |
| 8,347,891 B2 | 1/2013 | Demarais et al. | |
| 11,844,565 B2 | 12/2023 | Asirvatham | |
| 2001/0007938 A1 | 7/2001 | Long | |
| 2002/0029062 A1 | 3/2002 | Satake | |
| 2002/0087156 A1 | 7/2002 | Maguire et al. | |
| 2002/0198521 A1 | 12/2002 | Maguire | |
| 2003/0050637 A1 | 3/2003 | Maguire et al. | |
| 2003/0078575 A1 | 4/2003 | Jahns et al. | |
| 2003/0144658 A1 | 7/2003 | Schwartz et al. | |
| 2003/0225338 A1 | 12/2003 | Altman | |
| 2004/0006333 A1 * | 1/2004 | Arnold | A61L 29/085 606/15 |
| 2004/0054360 A1 * | 3/2004 | Schwartz | A61B 18/24 606/7 |
| 2004/0098030 A1 | 5/2004 | Makower et al. | |
| 2004/0106952 A1 | 6/2004 | Lafontaine | |
| 2004/0199155 A1 * | 10/2004 | Mollenauer | A61B 18/08 604/113 |
| 2004/0215177 A1 | 10/2004 | Swanson | |
| 2005/0096647 A1 * | 5/2005 | Steinke | A61B 18/1815 606/41 |
| 2005/0273095 A1 | 12/2005 | Taimisto et al. | |
| 2006/0111701 A1 | 5/2006 | Oral et al. | |
| 2006/0224153 A1 | 10/2006 | Fischell et al. | |
| 2006/0229659 A1 * | 10/2006 | Gifford | A61B 17/221 606/200 |
| 2007/0021746 A1 | 1/2007 | Taimisto et al. | |
| 2007/0066864 A1 * | 3/2007 | Forde | A61B 18/1815 606/213 |
| 2007/0083192 A1 | 4/2007 | Welch | |
| 2007/0149963 A1 | 6/2007 | Matsukuma et al. | |
| 2007/0225800 A1 | 9/2007 | Sahtjian | |
| 2007/0250050 A1 | 10/2007 | Lafontaine | |
| 2007/0287886 A1 | 12/2007 | Saadat | |
| 2008/0009747 A1 | 1/2008 | Saadat et al. | |
| 2008/0086073 A1 | 4/2008 | McDaniel | |
| 2008/0249463 A1 | 10/2008 | Pappone | |
| 2008/0306570 A1 | 12/2008 | Rezai | |
| 2009/0062790 A1 | 3/2009 | Malchano et al. | |
| 2009/0228003 A1 | 9/2009 | Sinelnikov | |
| 2009/0247933 A1 | 10/2009 | Maor | |
| 2010/0125239 A1 | 5/2010 | Perry et al. | |
| 2010/0145306 A1 | 6/2010 | Mickley et al. | |
| 2010/0249702 A1 | 9/2010 | Magana et al. | |
| 2010/0256629 A1 | 10/2010 | Wyle et al. | |
| 2010/0286684 A1 | 11/2010 | Hata et al. | |
| 2011/0060331 A1 | 3/2011 | Ibrahim et al. | |
| 2011/0276047 A1 | 11/2011 | Sklar et al. | |
| 2012/0095395 A1 | 4/2012 | Haery | |
| 2012/0143099 A1 | 6/2012 | Daniels et al. | |
| 2013/0012866 A1 | 1/2013 | Deem et al. | |
| 2013/0012938 A1 | 1/2013 | Asirvatham et al. | |
| 2013/0066312 A1 | 3/2013 | Subramaniam | |
| 2014/0005540 A1 | 1/2014 | Merhi | |
| 2014/0012242 A1 * | 1/2014 | Lee | A61B 18/02 606/21 |
| 2014/0371736 A1 | 12/2014 | Levin et al. | |
| 2015/0141917 A1 | 5/2015 | Tilson et al. | |
| 2016/0374754 A1 | 12/2016 | Asirvatham | |
| 2018/0360531 A1 | 12/2018 | Holmes et al. | |
| 2019/0336208 A1 | 11/2019 | Asirvatham | |
| 2024/0058057 A1 | 2/2024 | Asirvatham et al. | |

FOREIGN PATENT DOCUMENTS

| | | |
|---|---|---|
| WO | WO 2008/139232 A2 | 11/2008 |
| WO | WO 2009/036118 A1 | 3/2009 |
| WO | WO 2010/141417 A2 | 12/2010 |
| WO | WO 2012/114333 A1 | 8/2012 |
| WO | WO 2014/189887 | 11/2014 |

OTHER PUBLICATIONS

PCT International Preliminary Report on Patentability in International Appln. No. PCT/US2016/58629, dated May 1, 2018, 7 pages.
PCT International Search Report and Written Opinion in International Appln. No. PCT/US2016/58629, dated Mar. 2, 2017, 16 pages.
European Office Action in European Appln. No. 14801752.8, mailed on Feb. 6, 2019, 5 pages.
Extended European Search Report in Eropean Appln. No. 14801752.8, mailed on Sep. 11, 2017, 15 pages.
Gray et al., "Drug-coated balloons for the prevention of vascular restenosis," Circulation, Jun. 2010, 121(24):2672-2680.
PCT International Preliminary Report on Patentability for PCT/US2014/038722, mailed on Dec. 3, 2015, 10 pages.
PCT International Search Report and Written Opinion for PCT/US2014/038722, mailed on Dec. 11, 2014, 17 pages.
Supplementary European Search Report in European Appln. No. 14801752.8, mailed on Jun. 23, 2017, 17 pages.
Tyagi et al., "Hypertonic saline: a clinical review," Neurosurg. Rev., Jun. 2007, 30(4):277-290.
U.S. Appl. No. 14/892,035, filed Nov. 18, 2015, Samuel J. Asirvatham, Issued as U.S. Pat. No. 10,390,879.
U.S. Appl. No. 16/509,678, filed Jul. 12, 2019, Samuel J. Asirvatham, Issued as U.S. Pat. No. 11,844,565.
U.S. Appl. No. 18/386,872, filed Nov. 3, 2023, Samuel J. Asirvatham, Published as U.S. Publication No. 2024/0058057.

* cited by examiner

DEVICES AND METHODS FOR ABLATION OF TISSUE

CROSS REFERENCE TO RELATED APPLICATIONS

This application is a divisional application of U.S. application Ser. No. 15/771,593 filed on Apr. 27, 2018, which is a National Stage application under 35 U.S.C. § 371 of International Application No. PCT/US2016/058629, having an International Filing Date of Oct. 25, 2016, which claims the benefit of U.S. Provisional Application No. 62/247,048, filed Oct. 27, 2015. The disclosures of the prior applications are considered part of and are incorporated by reference in the disclosure of this application.

BACKGROUND

1. Technical Field

This document relates to devices and methods for the treatment of medical disorders including heart conditions and hypertension. For example, among other things this document relates to devices and methods for treating atrial fibrillation by performing thoracic vein ablation procedures, including pulmonary vein myocardium ablation. In some embodiments, the ablation procedures are performed in coordination with the delivery a pharmacological agent that can provide therapeutic effects such as the abatement of tissue stenosis or neointimal hyperplasia that may otherwise be caused by the ablation. Additionally, in some embodiments, particulate matter, such as thrombus or crystalline drug compounds, created during the ablation is captured and removed from the patient using devices and methods provided herein. Further, devices and methods for non-thermal methods of causing cell death, such as tissue suction and tissue stretching, are also provided herein.

2. Background Information

Atrial fibrillation is an irregular and often rapid heart rate that commonly causes poor blood flow to the body. During atrial fibrillation, the heart's two upper chambers (the atria) beat chaotically and irregularly—out of coordination with the two lower chambers (the ventricles) of the heart. Atrial fibrillation symptoms include heart palpitations, shortness of breath, and weakness.

Ablation procedures, including ablation of thoracic veins such as the pulmonary vein, are a treatment for atrial fibrillation. During pulmonary vein ablation, catheters are inserted into the atrium. Energy is delivered from the catheter to the tissue of the pulmonary vein and/or near the ostia of the pulmonary veins in the left atrium. The energy delivered causes scarring of the tissue. The scars block impulses firing from within the pulmonary veins, thereby electrically "disconnecting" them or "isolating" them from the heart. This can provide restoration of normal heart rhythms.

However, an undesirable side effect of treatment of atrial fibrillation by pulmonary vein ablation is pulmonary vein stenosis and neointimal hyperplasia. Pulmonary vein stenosis is the narrowing of the vessels that carry blood from the lungs to the heart. Pulmonary vein stenosis can result in reduced cardiopulmonary efficiency and a decline in quality of life. In some cases, to reduce the effects of stenosis, only a partial circumference of the pulmonary vein is ablated. However, such partial-circumferential ablation procedures are generally less effective for eliminating atrial fibrillation in comparison to ablation of the entire circumference of the pulmonary veins and/or pulmonary vein ostia.

In some cases, ablation procedures can also be used advantageously in the renal arteries to treat hypertension. Ablation of the renal sympathetic nerves using catheter-delivered radiofrequency energy may be an effective intervention for uncontrolled hypertension in some instances. For example, such renal denervation procedures may be beneficial for at least some of the 20 to 30 percent of adults being treated for hypertension that do not achieve adequate blood pressure control with medications.

SUMMARY

This document provides devices and methods for treating atrial fibrillation, hypertension, and other medical disorders. Atrial fibrillation can be treated in accordance with the devices and methods provided herein by performing a transcatheter ablation procedure, including a pulmonary vein myocardium ablation procedure. In some embodiments, the ablation can be performed in temporal coordination with the delivery of a pharmacological agent to reduce the occurrence of vein stenosis or neointimal hyperplasia. In some embodiments, the pharmacological agent may be embodied in a coating on the surface of a balloon device that makes contact with the tissue receiving treatment. In particular embodiments, the pharmacological agent may be initially contained within a balloon device and then exuded through the surface of the balloon device to the tissue receiving treatment. Additionally, in some embodiments, particulate matter, such as thrombus or crystalline drug compounds, created during the ablation is captured and removed from the patient using devices and methods provided herein. Further, devices and methods for non-thermal methods of causing cell death, such as tissue suction and tissue stretching, are also provided herein.

In one implementation, a catheter-based system for treating a tissue includes an ablation catheter device and a catheter defining a lumen. The ablation catheter device is slidably disposed within the lumen. The catheter includes an expandable distal end portion. The ablation catheter device includes an elongate catheter shaft including a liquid delivery lumen therethrough, a balloon device disposed at a distal end portion of the catheter shaft, and one or more electrodes that are disposed on or within the balloon device and are arranged to deliver energy to the tissue. The balloon device includes an outer surface and an inner surface. The inner surface defines an interior space of the balloon device. The balloon device is in fluid communication with the liquid delivery lumen. The balloon device includes a porous or microporous material that is arranged to transmit a liquid through the porous or microporous material.

Such a catheter-based system may optionally include one or more of the following features. The one or more electrodes may be a single electrode disposed on the catheter shaft and in the interior space. The one or more electrodes may be a plurality of electrodes disposed on the outer surface. The plurality of electrodes may include at least one electrode that is arranged to transmit radio frequency energy for ablation of the tissue and at least one electrode that is arranged to transmit direct current electrical energy. The one or more electrodes may include (i) a single electrode disposed on the catheter shaft and in the interior space and (ii) plurality of electrodes disposed on the outer surface. The single electrode may be arranged to transmit radio frequency energy for ablation of the tissue. The plurality of electrodes may include at least one electrode that is arranged to transmit direct current electrical energy.

In another implementation, a method for treating a tissue of a patient includes inserting a catheter-based system into the patient, deploying the ablation catheter device near the tissue, expanding the expandable distal end portion, deploying the expanded expandable distal end portion against a tissue wall to enclose a space adjacent at least a portion of the ablation catheter device, supplying ablation energy to the ablation catheter device and suctioning the space via the catheter. The catheter-based system includes an ablation catheter device, and a catheter defining a lumen. The ablation catheter device is slidably disposed within the lumen, the catheter including an expandable distal end portion.

Such a method for treating a tissue of a patient may optionally include one or more of the following features. The tissue may be a pulmonary vein. The tissue may be a renal artery. The method may further include, after the suctioning, irrigating the space with an irrigant supplied via the catheter. The method may further include, after the irrigating, suctioning the space via the catheter.

In another implementation, a catheter-based system for treating a tissue includes a double-balloon catheter. The double-balloon catheter includes a catheter shaft, a proximal inflatable member attached to the catheter shaft, and a distal inflatable member attached to the catheter shaft at a location that is distally spaced apart from the proximal inflatable member. The catheter shaft includes a lumen that defines an opening at a location between the proximal inflatable member and the distal inflatable member.

Such a catheter-based system may optionally include one or more of the following features. The system may also include a delivery sheath defining a lumen, wherein the double-balloon catheter is slidably disposed within the lumen.

In another implementation, a method for treating a tissue of a patient includes inserting a double-balloon catheter into a vessel of the patient, expanding the proximal inflatable member within the vessel, expanding the distal inflatable member within the vessel, wherein a space is defined by a vessel portion located between the expanded proximal inflatable member and the expanded distal inflatable member, and after expanding the proximal inflatable member and the distal inflatable member, suctioning the space via the catheter to collapse the vessel portion to a smaller than normal diameter. The catheter-based system includes an ablation catheter device, and a catheter defining a lumen. The ablation catheter device is slidably disposed within the lumen. The catheter includes an expandable distal end portion.

Such a method for treating a tissue of a patient may optionally include one or more of the following features. The tissue may be a pulmonary vein. The tissue may be a renal artery. The method may also include supplying ablation energy to the space via the double-balloon catheter.

In another implementation, a method for treating a tissue of a patient includes inserting a double-balloon catheter into a vessel of the patient, expanding the proximal inflatable member within the vessel, expanding the distal inflatable member within the vessel (wherein a space is defined by a vessel portion located between the expanded proximal inflatable member and the expanded distal inflatable member), and after expanding the proximal inflatable member and the distal inflatable member, supplying a fluid to the space via the catheter to expand the vessel portion to a larger than normal diameter. The double-balloon catheter includes a catheter shaft, a proximal inflatable member attached to the catheter shaft, and a distal inflatable member attached to the catheter shaft at a location that is distally spaced apart from the proximal inflatable member. The catheter shaft includes a lumen that defines an opening at a location between the proximal inflatable member and the distal inflatable member.

In some embodiments, the method also includes supplying ablation energy to the space via the double-balloon catheter.

Particular embodiments of the subject matter described in this document can be implemented to realize one or more of the following advantages. Medical conditions such as atrial fibrillation, hypertension, and others can be effectively treated using the devices and methods provided herein. In some embodiments, atrial fibrillation can be treated by pulmonary vein ablation while preventing or reducing stenosis or neointimal hyperplasia of the pulmonary veins by providing a temporally coordinated delivery of an antimitotic pharmacological agent to the pulmonary vein during the ablation procedure. In some embodiments, the uptake of the antimitotic pharmacological agent to the tissue receiving the ablation treatment can be promoted using the methods and devices provided herein. In some embodiments, fibrosis can be advantageously promoted to treat various medical conditions. In some embodiments, embolic protection is provided by integrating a hood device or a filter device with the ablation devices provided herein. In some embodiments, an occlusive member is integrated with the ablation devices to inhibit or prevent residual blood flow around or past the devices. In some such embodiments, the ablation treatment and/or the uptake of the antimitotic pharmacological agent to the tissue receiving the ablation treatment can be enhanced by substantially preventing blood flow around or past the devices. In some embodiments, the devices and methods provided herein can capture and remove particulate matter generated by the ablation process. Such particulate matter may otherwise potentially become harmful emboli. Devices and methods for applying tissue suction and/or expansion to porate cells and cause irreversible cell death are also provided herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1A:
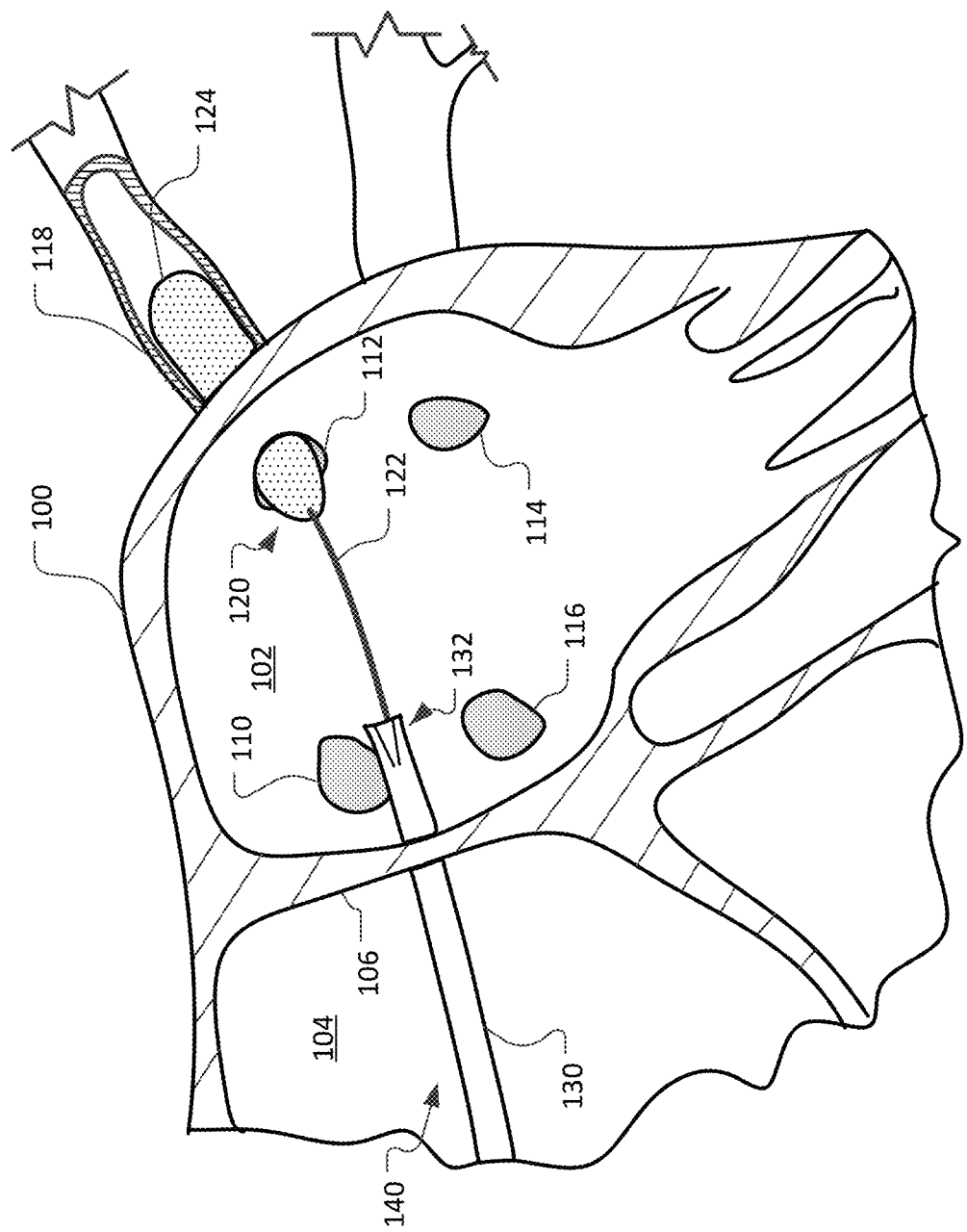
FIG. 1A is a schematic diagram of a heart and a partially deployed system for pulmonary vein ablation in accordance with some embodiments provided herein.

This document provides devices and methods for the treatment of heart conditions, hypertension, and other medical disorders. For example, among other things this document provides devices and methods for treating atrial fibrillation by performing a transcatheter pulmonary vein myocardium ablation procedure and for reducing the occurrence of vein stenosis or neointimal hyperplasia by delivering a pharmacological agent to the tissue receiving the ablative energy in temporal coordination with the ablative energy. Additionally, in some embodiments, particulate matter, such as thrombus or crystalline drug compounds, created during the ablation is captured and removed from the patient using devices and methods provided herein. Further, devices and methods for non-thermal methods of causing cell death, such as tissue suction and tissue stretching, are also provided herein.

In some implementations, a pharmacological agent is delivered simultaneously with the application of the ablative energy. In some implementations, the pharmacological agent is delivered before or after the application of the ablative energy. In some implementations, the pharmacological agent is delivered using a combination of such temporal methods. In some implementations, a repetitious cycling of such methods are used. However, in some implementations, no delivery of a pharmacological agent is administered directly by the ablation devices provided herein. Rather, in such implementations ablative energy is delivered without the delivery of a pharmacological agent from the ablation device.

In some implementations that include the delivery of a pharmacological agent, the pharmacological agent may include a crystalline compound. That is, some pharmacological agents used in conjunction with the ablation procedures described herein may be an irrigation of a drug such that some crystalline particulate may be released during or after the delivery of the ablative energy and drug administration. Some embodiments of catheter-based ablation systems provided herein include a hood catheter that, as described further below, can be used to locally capture and remove such crystalline particulate and/or other types of particulate, thereby preventing emboli from being in the patient's vasculature.

The catheter-based ablation systems provided herein that include a hood catheter can also function to remove of coagula such as, but not limited to, thrombus formed in conjunction with the ablation process. As described further below, the coagula can be captured within the confines of the hood catheter and suctioned out of the patient's blood stream. Further, in some cases, one or more cycles of aspiration, irrigation, and re-aspiration may be implemented using the devices and methods provided herein. In some embodiments, emboli can be mechanically alternatively or additionally captured by the hood catheter in a localized manner (near to the source of the emboli). While the hood devices described herein are illustrated in the context of pulmonary vein ablation, it should be understood that the hood devices can be used in many other contexts such as, but not limited to, the mitral valve (repair or replacement), VT ablation, any left-heart ablation procedure, and the like.

In some embodiments, the hood catheter devices provided herein can be deployed on another catheter device on an as-needed basis. For example, if a catheter device has thrombus attached thereto, a hood catheter device can be deployed over the catheter and used to capture and contain the thrombus, or to remove the thrombus from the catheter by aspiration. In some embodiments, the hood catheter can be deployed over a guidewire.

While the devices and methods provided herein are primarily described in the context of the treatment of pulmonary veins to mitigate atrial fibrillation, many other bodily areas and medical conditions may be treated using the concepts provided. For example, the devices and methods provided herein may also be used to treat other thoracic veins, including the superior vena cava, left superior vena cava or its remnants, the azygos vein, and other venous structures. In another example, the devices and methods provided herein may also be used to treat other endocardial tissues in the atria or ventricles. In still another example, the devices and methods provided herein may also be used to treat the renal arteries as part of a renal denervation procedure. In addition, the devices and methods provided herein may also be used to treat bodily areas and medical conditions including but not limited to: pulmonary hypertension, appendage ablation; aortic coarctation; esophageal stenosis; bronchial tree, GI lumen and stenotic valve disorders; great vessel ablation for ventricular arrhythmia—as a handheld device for treating skin conditions including hemangiomas, burns, and wrinkles; the retroglossal region—to stiffen tissue and/or treat sleep apnea; peripheral vessels and coronary arteries—to "cholesterol proof" vessels and/or prevent atherosclerosis; gastric vessels or celiac—to lower ischemic threshold so satiety is felt earlier; coronary vessels—to treat vasospasm; heriorrhaphy or hernia repair, and cerebral vessels—to treat migraine. Still further, the devices provided herein may be used for a preventative treatment for coronary atherosclerosis, especially in the left main, proximal LAD, and proximal circumflex. That is, when used in combination with either a lipolytic agent or a calcilytic agent (e.g., diethyl ether) this technique can be used to treat coronary vascular legions. A further application of the devices and methods provided herein is retrouterine access to the fallopian tubes to treat stenosis, for example resulting from inflammatory disease, to keep the lumen open and the endothelium non-disrupted so that fertility is kept intact. Still further, the devices and methods provided herein can be used for creating (e.g., using DC electroporation) or remedially-treating transseptal punctures (e.g., of the atrial septum).

In addition, in some implementations the devices and methods provided herein can be used to treat certain conditions by ablating tissue while beneficially allowing or promoting a controlled and desirable level of fibrosis. In some implementations, a pharmacological agent that promotes fibrosis can be used. For example, urinary incontinence can be treated by fibrosing the urethral wall in a controlled manner. This technique can also be used to close lumens in some situations like diverticulae, aneurysms, and pseudoaneurysms. This technique can also be used to narrow or to completely sclerose the ostium of the left atrial appendage (LAA). In some cases, narrowing the ostium of the LAA will increase blood flow velocity thereby making stasis and thrombus less likely. Further, pulmonary bullae can also be treated by promoting fibrosis with an appropriate agent such as copper, and using a balloon device such as the example balloon device embodiments provided herein. In another example, varicose veins can be treated using a fibrosing agent combined with ablation energy to drive the agent into the vessel walls, in accordance with the devices and methods provided herein.

Further, in some implementations the devices and methods provided herein can be used to abate the development of atheroma within arterial vessels. That is, in some cases the negative effects of cholesterol in the coronary arteries or major vasculature can be reduced. In some implementations, the devices and methods provided herein can be used to stabilize existing atheroma, thereby making rupture of atheroma less likely.

Still further, in some implementations the devices and methods provided herein can be used to provide pulmonary veno-occlusive disease therapy and/or to treat fibrosing mediastinitis. For example, devices as described herein can be designed to be disposed within and securely seated in the pulmonary vein. The secured device provides a vantage point for deploying a small wire with an over-the-wire expandable balloon that can be inflated to treat the walls of the pulmonary veins much deeper than the position of the secured device. In some cases, the over-the-wire expandable balloon can be positioned anywhere from the pulmonary vein ostia to the lung capillaries. A drug from a coating on over-the-wire expandable balloon (or from within a balloon) could thereby be delivered. Alternatively, or additionally, in some cases such a device can be used to deliver a biodegradable stent with an anti-inflammatory/anti-neoplastic drug to the area for more sustained therapy. Moreover, such an over-the-wire expandable balloon could also be used to deliver low dose electroporation to further enhance drug uptake into the walls of the pulmonary veins. For example, the delivery of antiproliferative agents can be facilitated and/or driven using such electroporation.

Another advantageous application of the devices and methods described herein is for retrieval or repositioning of pulmonary stent devices. Such a procedure can be performed using an emboli-capturing hood device (as described herein). This would give the operator an opportunity for improved patient safety by: (i) preventing any dislodged thrombus or debris that gets dislodged from entering into the left-sided circulation (would get entrapped in the hooded device) and (ii) providing an oversheath so that the stent can be safely grabbed and then safely retrieved and removed within the hooded device to prevent any damage to adjacent structures. Additionally, such a technique can provide the ability to deliver a covered stent in the case of pulmonary vein tear/rupture where immediate tamponade would be necessary.

The hood devices described herein can also be used to reduce or prevent complications in the case of using a circular mapping catheter. For example, the hood device can be used for containment of such a mapping catheter, and thus prevent undesired catheter interactions with and/or entrapment in the mitral valve.

Some implementations of the devices and techniques described herein can include optimizing electrical ostium identification and prevention of pulmonary vein ablation. That is, some embodiments provide an added functionality of preventing pulmonary vein ablation when it is not desired (e.g., when ablating the antrum or atria encircling the pulmonary vein ostia). This can be particularly useful since some implementations include a radiofrequency (RF) ablation in combination with electroporation. (e.g., for delivering RF ablation at/near the PV ostium). Accordingly, a highly effective approach of direct PV ablation (electroporation within the PVs) and safe RF ablation outside of the veins for WACA ("wide area circumferential ablation") lines. Thus, such an arrangement provides two safeguards to prevent any re-connection. In some embodiments, such a device can be designed by multi-planar electrodes on two separate balloons. In one example, one of the balloons would be positioned inside the pulmonary vein (for securing and stability—but more so important for the electrodes to show a sharp pulmonary vein potential defining the ostium and inside of the pulmonary vein). The electrodes on the balloon which are abutting the left atrium around the ostium (outside of the PV ostium) could have delay of the left atrial signal and the pulmonary vein potential and thus a safe place for RF delivery. In some embodiments, there could be a feedback loop for safety so that energy would never be delivered if the electrogram has no ostial delay between LA and PV signals (e.g., in some embodiments this can be an algorithm with feedback loop). One of the balloons acts a "safety marker" (whereby ablation does not occur at that location and only proximal lesions to the balloon are allowed). Such a device design can also help in some cases with ablation at difficult antrum or carina where it would be undesirable to slip into a pulmonary vein.

In some embodiments, the devices and techniques described herein allow for using a combination of RF and DC electroporation energy to provide safer ablation on or near the posterior heart wall with adjacencies of an esophagus and/or phrenic nerve. For instance, when close to the esophagus, the energy delivery can be switched from RF energy to DC electroporation to prevent thermal damage to the esophagus. In a similar manner, for example in regard to ablation of the superior vena cava (without limitation), the ability to pace to define the phrenic nerve course and to switch over to DC electroporation can be included in the devices described herein. Similarly the suction component of the devices can be utilized to pull the left atrial structure away from the esophagus if necessary. Further, the double balloon devices described herein can be advantageously used as an insulating means for separation of energy (e.g., with a balloon serving as a barrier from tissue adjacent to phrenic nerve).

It should be understood that, some of the concepts disclosed herein provide to a target area of the body the temporally coordinated delivery of: (i) tissue-ablative energy and, in some embodiments (ii) an antimitotic/antifibrotic pharmacological agent to abate the generation of stenosis and/or neointimal hyperplasia that may be caused by the delivery of the tissue-ablative energy. For example, this document discloses a variety of multi-functional balloon catheter embodiments, and methods for their use. These balloon catheters include one or more ablative energy sources, as well as the ability to deliver a pharmacological agent (in some embodiments) for the prevention or reduction of vessel stenosis and neointimal hyperplasia. Those device embodiments that are capable of delivering a pharmacological agent may do so using a variety of delivery modalities. For example, in some embodiments the pharmacological agent may be embodied in a coating on the surface of a balloon device that makes contact with the tissue receiving treatment. In particular embodiments, the pharmacological agent may be initially contained within a balloon device and then exuded through the porous or microporous surface of the balloon device to the tissue receiving treatment. In other device embodiments described below (e.g., refer to FIGS. 5A, 5B, 6A, and 6B), an expandable tubular framework with surface electrodes is used to deliver ablation energy to target tissue. In some such embodiments, the tubular framework can be used as conduit(s) to convey a pharmacological agent to the tissue.

The coordinated delivery of ablative energy and anti-stenosis drugs can facilitate an effective treatment of atrial fibrillation and other medical conditions. One contributing factor to the efficacy of the treatment is that it can allow the entire circumference of the pulmonary veins and/or pulmonary vein ostia to be ablated in conjunction with a lessened potential of causing pulmonary vein stenosis. In contrast, some other ablation procedures ablate only a partial circumference of the pulmonary veins to reduce the potential of causing pulmonary vein stenosis. Such partial-circumferential ablation procedures may have a lower efficacy of treating atrial fibrillation as compared to the methods described herein. That is the case, for example, because the delivery of the anti-stenosis pharmacological agent along with the ablation energy facilitates ablation of an entire circumference of the pulmonary veins and/or pulmonary ostia using the devices and methods provided herein.

While various embodiments of balloon catheters for delivering ablative energy are described herein, it should be understood that other types of ablation devices can be used with some embodiments of the ablation systems provided herein. For example, such types of ablation devices can include, but are not limited to, catheters, probes, pads, wands, matrices, jawed devices, and the like. Hood catheters, such as described herein, can be used in conjunction with all such ablation devices. In some embodiments, the hood catheter is integrated with the ablation device such that a single transcatheter device/system is needed for the treatment and emboli capture. In some embodiments, the hood catheter is embodied as a separate device from the ablation device (but the two are used together for the procedure).

While the embodiments described herein are disclosed as providing specific types of ablation, it should be understood that a variety of ablation techniques and ablative energy sources are envisioned for use in combination with any of the devices provided herein. For example, monopolar or bipolar ablation techniques can be used. Ablation energy sources such as radiofrequency (RF), direct current (DC), alternating current (AC) in non-cardiac applications, cryogenics, hot solutions, and the like, and combinations thereof, can be used with the devices provided herein. In some embodiments, both DC and RF electrodes can be advantageously used in combination on the balloon devices provided herein. That is, RF electrodes may be included because they are well-suited for delivering ablation energy, while DC electrodes may also be included because they are well-suited as iontophoretic sources for driving the pharmacological agents into tissue. The use of DC and RF electrodes in combination can thereby provide a device that provides the benefits of both types of electrodes. In some embodiments, the same energy source used for ablation can be used to drive the medication/antifibrotic agent into the tissue. However, in some embodiments DC and a magnet-driven gradient can be used to drive the particles into the tissue as well. The carrier molecule for the antifibrotic agent may serve as an elution agent as well as a reservoir so that there is a long-term deployment of a stenosis-preventing agent. This may also enable noninvasive ablation by targeting the metallic particles that were driven into the vessel wall.

In some embodiments, the electrodes for delivery of the ablation energy are located on the exterior surface of the ablation devices. In other embodiments, one or more central electrodes are located on a central shaft within the interior space of a balloon ablation device. In those cases, in some embodiments the energy from the central electrode(s) can be transmitted to the target tissue by the liquid pharmacological agent that bathes the central electrode(s) and that exudes, elutes, weeps, or is otherwise transmitted from within the balloon to the tissue outside of the balloon. In some embodiments, a combination of types of electrodes are included in a single balloon device.

Another balloon embodiment includes spikes or spindles on the balloon's outer surface that are arranged to wedge into and temporarily anchor in relation to the surrounding tissue (e.g., myocardial tissue). These spikes or spindles can be metallic or made of the same material as the balloon itself. Some such embodiments have a balloon in a balloon, with the inside balloon being used to push the spindles out into engagement with the vessel or tissue surface/wall.

Another balloon embodiment has a natural (inflated) shape that is configured to be placed in the left atrial appendage. An ablation can be performed on a wide ring at the ostium of the appendage to electrically isolate the appendage in a simple, straightforward manner. When the balloon is still inside the appendage it is used as a marker. Epicardial access can be attained and clip electrodes can be placed on the left atrial appendage, as well as the right atrial appendage. This technique provides a stroke prevention therapy where the appendages will be stimulated, but because they are isolated, even if atrial fibrillation were to occur, the atrium will not fibrillate. This technique may provide the benefit that the muscle of the appendage can still be utilized to contribute to left atrial filling, which in turn may contribute to left ventricular filling, despite the presence of atrial fibrillation.

Some embodiments include an inner balloon within an outer balloon. A lumen of a catheter shaft is in fluid communication with the inter-balloon space between the inner and outer balloon. A drug can be delivered through the lumen and into the inter-balloon space. In coordination with the delivery of the drug, electrical or other types of energy can be delivered at a surface of either or both of the balloons, or at a location therebetween via electrodes within the inter-balloon chamber. Such a design can also advantageously allow different design and performance characteristics for the two balloons.

Some embodiments can have electrodes on the balloon for recording and/or pacing. Such electrodes can be located, both proximally and distally on the balloon, as well as, in some cases, along the balloon's length. This arrangement can advantageously enable the use of algorithms that employ impedance measurements and electrogram-derived signals to preferentially deliver dosages of the electroporation/ablation energy and/or drugs (e.g., antiproliferative agents, etc.) in relation to deliveries of the energy and vice versa (e.g., more energy at certain electrogram sites and more drug at other sites). Additionally, in some embodiments the timing of electroporation/ablation energy can be determined in part based on QRS cycles from recording electrodes on the device. For example, in some cases delivery of energy pulses (including, but not limited to, high frequency pulses) can be timed for delivery soon after the QRS is seen within the ventricular refractory period. Other techniques for timing or adjusting the delivery of electroporation/ablation energy pulses based on QRS cycles captured from recording electrodes on the devices provided herein can also be used. In some cases, this technique can be advantageous compared to relying on surface ECGs.

The embodiments described herein include provisions for the exudation and elution of a liquid pharmacological agent for the prevention or reduction of vessel stenosis and neointimal hyperplasia. For instance, the drug paclitaxel is an example of one type of an antimitotic pharmacological agent that can be delivered to the tissue undergoing ablation to prevent or reduce fibrosis and stenosis of the tissue. Paclitaxel can be used beneficially because of its rapid uptake and prolonged retention. In some implementations, paclitaxel can be delivered in 3% saline (or similar hypertonic solution) to further enhance its uptake and retention. While paclitaxel is provided as an example, other pharmacological agents can also be used. In some implementations, fine metal components (e.g., gold or tungsten) can be combined with the liquid pharmacological agents to form a barrier thereby preventing the agent from leaking out of the tissue. In other implementations, a high-energy DC shock (e.g., about 2 to 250 Joules) can be applied to the tissue during and/or after exuding the agent to effectively push the agent into the tissue.

The balloon devices provided herein can include materials of construction that are porous or microporous. As such, the balloons can allow exudation, elution, or weeping of liquid pharmacological agents from within the interior space of the balloon to the exterior surface of the balloon. In some embodiments, the balloon can comprise a balloon within a balloon, with the liquid pharmacological agent disposed in the cavity between the two balloons. This configuration can be used, for example, to reduce the required volume of liquid pharmacological agent within the balloon device. In some embodiments, the balloon devices provided herein, as an alternative to or in addition to being porous, can be coated with a pharmacological agent. Such coatings can be disposed on the surface of the balloon to make contact with the tissue, or near the tissue, that receives ablative energy from the electrodes of the balloon devices. The pharmacological agent coated on the balloon surface can thereby transfer to the tissue to provide a therapeutic effect.

FIG. 1A is a schematic diagram of a portion of a heart 100 that, as described further below, will undergo a pulmonary vein ablation procedure using a catheter-based ablation system 140 in accordance with some embodiments provided herein. Catheter-based ablation system 140 includes a balloon catheter ablation device 120 and a transseptal introducer sheath 130. Balloon catheter ablation device 120 is slidably disposed within a lumen defined by transseptal introducer sheath 130.

Catheter-based ablation system 140 is configured for percutaneous or minimally-invasive deployment techniques. Both balloon catheter ablation device 120 and transseptal introducer sheath 130 are individually controllable by a clinician ex vivo of the patient. In some cases, fluoroscopy or other imaging techniques are used by the clinician during the deployment and/or ablation procedure.

In general, balloon catheter ablation device 120 includes a multi-lumen catheter shaft 122 connected to a balloon device 124. In some embodiments, the proximal end of balloon catheter ablation device 120 is connected to an ablation energy source and controller (e.g., an RF generator system not shown) and a liquid pharmacological agent source (not shown), both of which are located external to the patient. Balloon device 124 is located at the distal end of catheter shaft 122. An interior space of balloon device 124 is in fluid communication with a liquid delivery lumen of catheter shaft 122. The liquid delivery lumen is used to convey the liquid pharmacological agent from the source external to the patient into the interior space of balloon device 124.

In some example implementations, the distal end of catheter-based ablation system 140 can be positioned in a left atrium 102 of heart 100 according to standard techniques. For instance, using an example standard technique, catheter-based ablation system 140 can enter a right atrium 104 of heart 100 through a femoral vein and the inferior vena cava (not shown). Catheter-based ablation system 140 can be passed through a puncture in an atrial septum 106 to access left atrium 102. From left atrium 102, balloon catheter ablation device 120 can be emerged from the lumen of transseptal introducer sheath 130 and positioned through any of the pulmonary vein ostia 110, 112, 114, or 116 to enter a pulmonary vein such as pulmonary vein 118 shown. In some cases, one or more radiopaque markers can be included on transseptal introducer sheath 130 and/or on balloon catheter ablation device 120 to assist with the radiographical visualization of the position of catheter-based ablation system 140 during delivery and deployment.

While this example implementation describes ablation of pulmonary vein 118, it should be understood that other tissues, including but not limited to other atrial or ventricular tissues, can receive the ablation treatment using the devices and techniques provided herein. Moreover, various other types of ablation devices (other than a balloon device) can be used to delivery the ablative energy, without departing from the scope of the disclosure provided herein.

With balloon catheter ablation device 120 positioned within pulmonary vein 118, in some implementations the next step is to inflate balloon device 124 using a liquid pharmacological agent as the inflation medium. Alternatively, in some implementations, prior to inflation of balloon device 124, an expandable distal end portion 132 of transseptal introducer sheath 130 is deployed into a generally conical shape and then positioned to surround a proximal portion of balloon catheter ablation device 120.

Figure 1B:
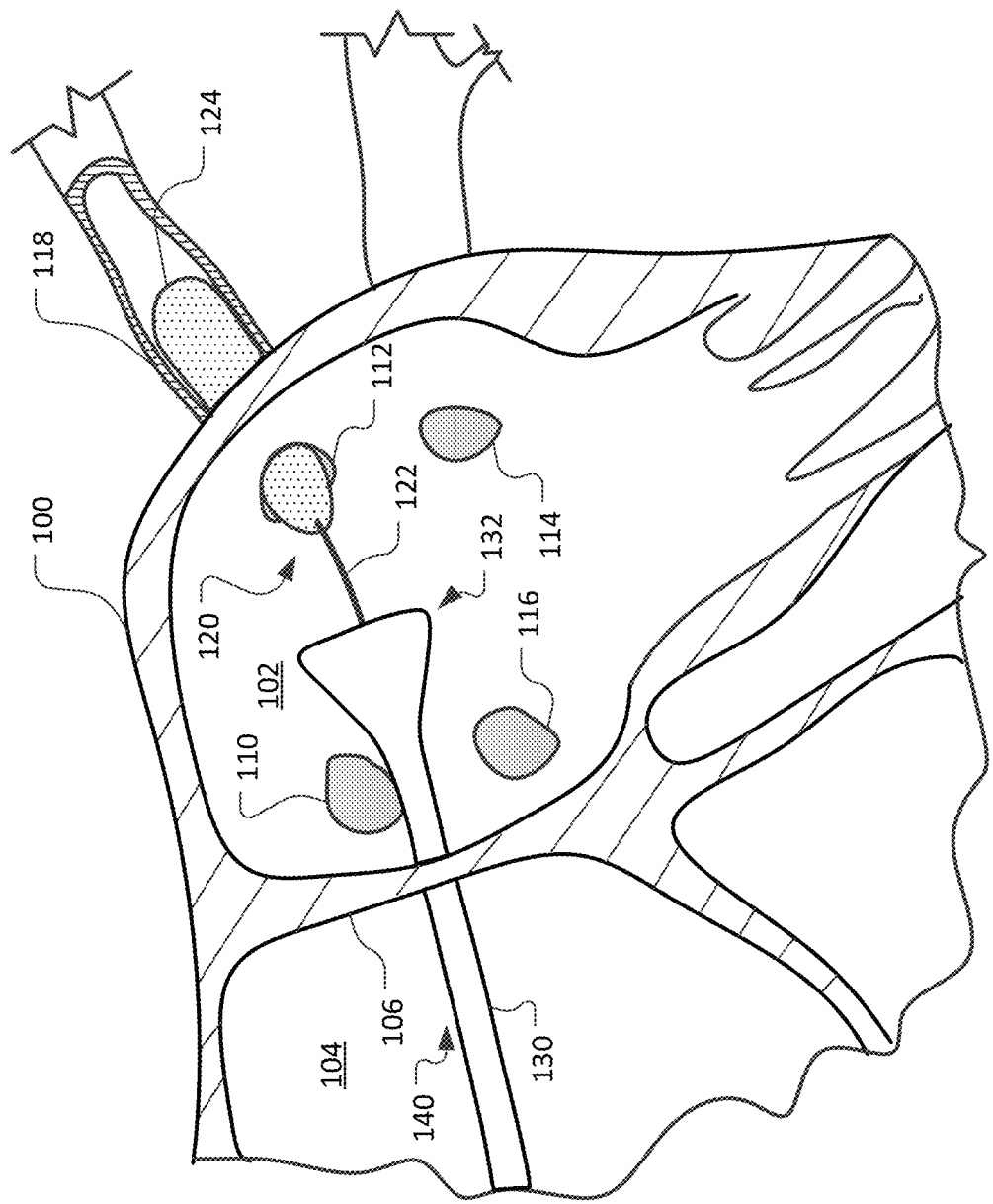
FIG. 1B is the schematic diagram of FIG. 1A showing another step in the deployment process of the system for pulmonary vein ablation.

Referring also to FIG. 1B, in some embodiments transseptal introducer sheath 130 includes expandable distal end portion 132. In some embodiments, expandable distal end portion 132 is selectively deployable by a proximally-located ex vivo deployment actuator. As expandable distal end portion 132 is deployed, it radially expands into a generally conical or frustoconical shape, such that an enlarged interior space is defined within expandable distal end portion 132. In some embodiments, expandable distal end portion 132 is expanded using mechanisms and techniques such as, but not limited to, inflation, shape-set materials (e.g., a nitinol frame), one or more control wires, mechanical linkages, and the like, and combinations thereof. In some embodiments, expandable distal end portion 132 may include one or more pleats, folds, elastic portions, and the like.

After the deployment of expandable distal end portion 132, transseptal introducer sheath 130 can be advanced to enclose the area to be treated by balloon catheter ablation device 120.

Figure 1C:
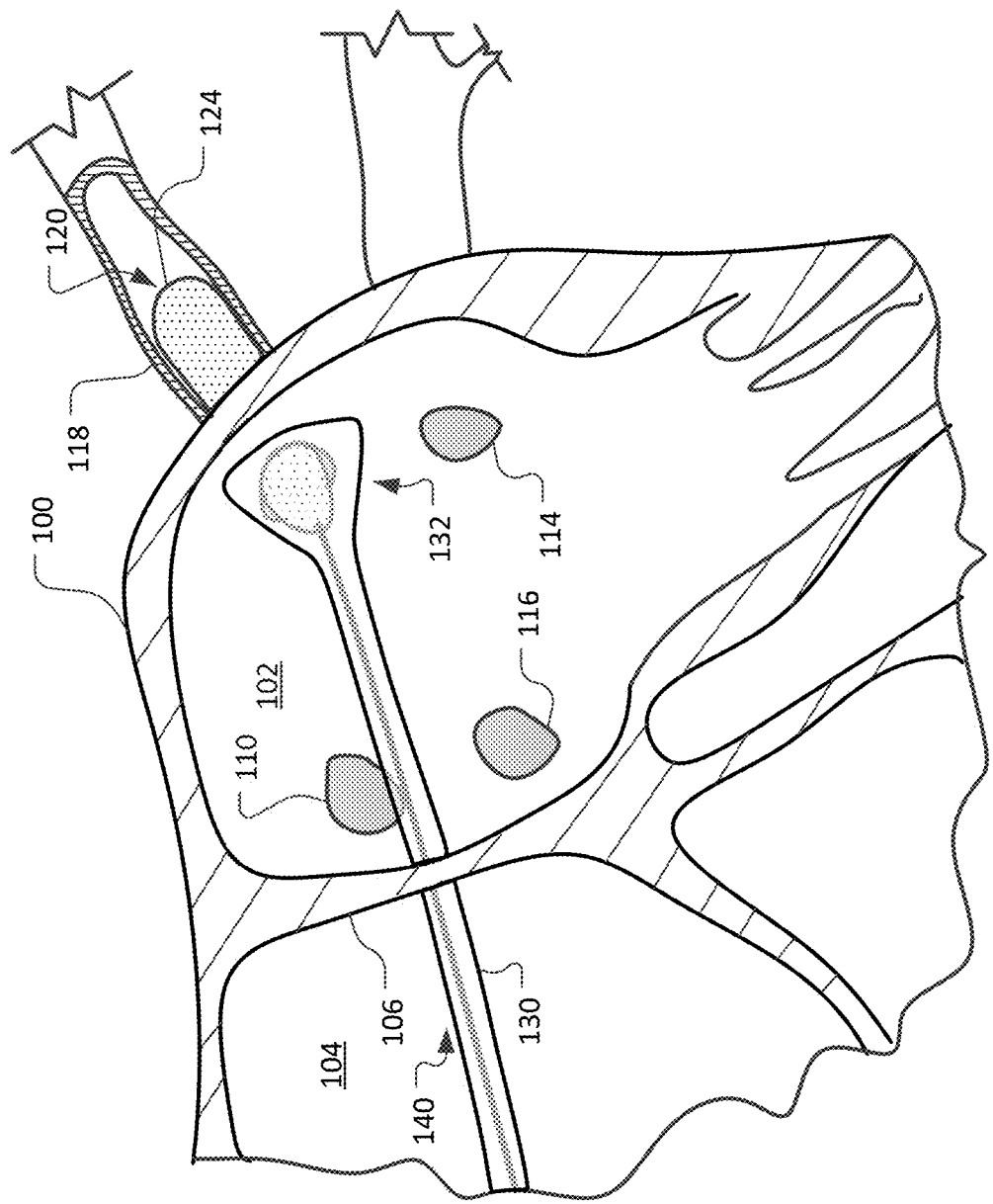
FIG. 1C is the schematic diagram of FIG. 1A with the system for pulmonary vein ablation fully deployed such that ablation and particulate capture can take place.

Referring also to FIG. 1C, with balloon catheter ablation device 120 positioned at the target site to be ablated, expandable distal end portion 132 can be distally advanced into contact with the tissue surrounding balloon catheter ablation device 120. In FIG. 1C, transseptal introducer sheath 130 is shown semi-transparently so that balloon catheter ablation device 120 can also be fully visualized. In the depicted arrangement, a volumetric space is defined between expandable distal end portion 132 and the wall of left atrium 102 (surrounding ostia 112).

In some embodiments, expandable distal end portion 132 includes features that adapt it to closely and/or sealably interface with the wall of left atrium 102. Such sealing and/or attachment can facilitate efficacious capture of emboli using expandable distal end portion 132. For example, in some embodiments expandable distal end portion 132 may be compliant so as to conform to non-planar topography of the wall of the left atrium 102. Additionally or alternatively, in some embodiments, expandable end portion 132 includes one or more vacuum applying elements that serve to suction expandable end portion 132 into sealed contact with the wall of left atrium 102. Mechanical elements (e.g., helical anchors and the like) can be included in some embodiments.

The inflation of balloon device 124 will cause the outer surface of balloon device 124 to make contact with the inner wall of pulmonary vein 118. In addition, the pressure of the liquid pharmacological agent inflation medium will cause some of the agent to exude, elute, weep, or otherwise be transmitted from within the interior space of the balloon 124 to the exterior surface of the balloon 124, and into contact with the inner wall of pulmonary vein 118.

In some cases, a crystalline drug solution is used as the liquid pharmacological agent inflation medium. In some such cases, crystalline particulate may be released into atrium 102. With the expandable distal end portion 132 in contact with the wall of left atrium 102 (surrounding ostia 112), such crystalline particulate may be captured and removed so that the potential emboli are not released into the patient's blood stream.

At this juncture, balloon catheter ablation device 120 can be energized with ablation energy to initiate the modulation of target neural fibers. An example ablation technique can be generally performed as follows. An electric field can be generated by the external source/controller and transferred through wires within one or more lumens of catheter shaft 122 to electrodes disposed on the surface of or within balloon device 124. The electric energy can be transmitted to the inner wall of pulmonary vein 118 directly from the electrodes on the surface of balloon device 124 or indirectly from the electrodes within balloon device 124 while being conducted via the liquid pharmacological agent that exudes from the exterior surface of balloon device 124. The electric field can modulate the activity along neural fibers within the wall of pulmonary vein 118 by at least partially denervating the tissue. In some examples, while the electric field for ablation is being applied, transmission of the liquid pharmacological agent from balloon device 124 to the tissue can be continued.

Various types of ablation/electroporation energy can be used with the devices and techniques provided herein. For example, in some embodiments an RF energy source can be used. In other embodiments, other types of energy can be used (e.g., DC, AC, cryogenic, microwave, laser, and the like). In some embodiments, a combination of such energy sources can be used within a single embodiment of ablation balloon device (e.g., RF and DC are used in combination is some embodiments). The ablation/electroporation energy can be monopolar or bipolar.

In some implementations, additionally or alternatively, bipolar ablation can be performed between the pulmonary vein 118 and the left atrial appendage of heart 100 and/or other bi-arterial or venous locations.

In some embodiments for bipolar ablation including electroporation, expandable distal end portion 132 serves as the return electrode. In other words, the tip of expandable distal end portion 132 can be a conductor or dielectric that serves as the anode (or as the cathode) and electroporation can be delivered from the balloon 124 to the electrode(s) of expandable distal end portion 132 or vice-versa.

In some embodiments, balloon device 124 can define a lumen through which a catheter or wire with one or more electrodes can be passed such that the one or more electrodes are positioned distally of balloon device 124. Using this technique, the distally positioned electrodes can be place into the distal pulmonary vein to serve as return electrodes for bipolar ablation/electroporation in conjunction with energy delivery from balloon device 124.

Multiphasic ablation/electroporation can be selectively delivered using the devices and methods provided herein. In result, extraneous effects on non-targeted structures can be reduced or eliminated in some cases. For example, multiphasic ablation/electroporation can be delivered to minimize extracardiac stimulation of structures such as, but not limited to, nerves and skeletal muscles. In addition, multiphasic energy delivery can be used to facilitate electroporation (i.e., driving of drug delivery into particular cells) while preventing tissue ablation (i.e., preventing damage to the particular cells). In the context of this disclosure, multiphasic ablation/electroporation should be understood to include variations to ablation/electroporation parameters such as, but not limited to, pulse width, pulse duration, pulse amplitude, activated electrodes, activated bipolar electrode pairs, two or more concurrently activated bipolar electrode pairs, current flow direction, polarity, electrode activation timing/patterns, and the like, and combinations thereof.

In some cases, such multiphasic ablation/electroporation can be controlled automatically. Moreover, in some cases of automatic control, locally sensed electrograms can be used as input to the controller. In that manner, multiphasic delivery can be automatically controlled and customized in accordance with the sensed electrograms. In some cases, such multiphasic ablation/electroporation can be controlled manually.

The ablation process can be performed simultaneously and concurrently with the delivery of an antimitotic pharmacological agent to the tissue receiving the ablation energy. Alternatively, the ablation process can be performed sequentially with the delivery of an antimitotic pharmacological agent to the tissue receiving the ablation energy. That is, the antimitotic pharmacological agent can be delivered first and the ablation process can take place thereafter. Or, the antimitotic pharmacological agent can be delivered after the ablation process. In some implementations, a combination of such techniques can be used. For example, the antimitotic pharmacological agent can be delivered before and during the ablation process, or before and after, and so on. In other embodiments, the balloon 124 is coated with a pharmacological agent that is absorbed into the tissue of the pulmonary vein 118. In still other procedures, no pharmacological agent is administered directly by the balloon catheter ablation device 120.

Such techniques for the coordination of the deliveries of the ablative energy and the pharmacological agents can provide advantageous results. For example, delivering the agent prior to the ablative energy can provide iontophoresis-like action to drive the agent farther into the tissue. In another example, delivering the ablative energy prior to the pharmacological agent can provide some electroporative disruption of the endothelial cell-to-cell junction, thus promoting the agent delivery. In some implementations, a repetitious cyclic delivery of ablative energy and the pharmacological agent can thereby further enhance uptake of the agent. In some implementations, the pharmacological agent can have an ionic base so as to optimize the ablative energy's ability to get the agent beyond the endothelium of the tissue.

Paclitaxel is an example of one type of antimitotic pharmacological agent that is well-suited for this application. This technique of coordinating the delivery of paclitaxel with the ablation process can prevent or reduce the occurrence of fibrosis, stenosis, and neointimal hyperplasia of the tissue undergoing ablation. In such fashion, stenosis of pulmonary vein 118 can be reduced or prevented while full-circumferential ablation of pulmonary vein 118 is performed. In some cases, an antiproliferative agent can be delivered/driven using the electroporation devices and techniques provided herein.

In some implementations, as a result of the ablation treatment, particulate matter of one or more types may be generated. Such particulate matter may be captured within the volume of blood defined in the space between expandable distal end portion 132 and the wall of left atrium 102. Hence, catheter-based ablation system 140 is configured to provide embolic protection. For example, expandable distal end portion 132 of transseptal introducer sheath 130 can capture blood clots, plaque, tissue fragments, shards or particles of pharmacological agents, coagulum, and the like. In some circumstances, some such emboli may be generated or may become embolic as a result of the use of balloon catheter ablation device 120 if not captured and removed by catheter-based ablation system 140.

In some implementations, prior to deflation of balloon catheter ablation device 120, the blood within the space between expandable distal end portion 132 and the wall of left atrium 102 is suctioned out (e.g., vacuum aspirated). Such suction can be used to ensure that any particulate (e.g., thrombus, crystalline drug compounds, etc.) that may be present in the blood within the space between expandable distal end portion 132 and the wall of left atrium 102 is removed from the patient's vasculature. In some implementations, after the initial suctioning, a rinse solution (e.g., saline) may be supplied into the space between expandable distal end portion 132 and the wall of left atrium 102, and thereafter suctioned out. Using such a rinse solution and procedure may serve to remove additional potential emboli. In some cases, the rinse procedure may be used a single time, or may be repeated two, three, four, or more than four times.

After the aspiration of particulate, balloon catheter ablation device 120 may be deflated and withdrawn into transseptal introducer sheath 130. Expandable distal end portion 132 can be collapsed into a low-profile configuration. In doing so, expandable distal end portion 132 can mechanically capture emboli in some cases. Then, catheter-based ablation system 140 can be withdrawn from the patient.

Expandable distal end portion 132 can be constructed of various materials and configurations, and can be constructed using various techniques. In some embodiments, expandable distal end portion 132 comprises an ePTFE material. In some such embodiments, one or more portions of expandable distal end portion 132 comprises a framework and/or mesh of Nitinol material. In some such embodiments, expandable distal end portion 132 comprises a polyester material, a polyurethane material, or another type of synthetic material.

In some embodiments, expandable distal end portion 132 is configured to substantially occlude blood flow around the region of balloon device 124 and pulmonary vein ostia 112. In some such embodiments, the pore size of expandable distal end portion 132 can be selected so that expandable distal end portion 132 will occlude all or substantially all blood flow therethrough. In this manner, particulate can be captured within the space between expandable distal end portion 132 and the wall of left atrium 102. Moreover, in this manner blood flowing between balloon device 124 and the inner wall of pulmonary vein 118 can be reduced or eliminated as desired. Similarly, blood flowing in the space between expandable distal end portion 132 and pulmonary vein ostia 112 can be reduced or eliminated as desired. By so controlling the blood flow using expandable distal end portion 132, the therapeutic efficacy of balloon catheter ablation device 120 can be enhanced in some circumstances. For example, in some circumstances the uptake of liquid pharmacological agents and/or the transfer of ablation energy from balloon catheter ablation device 120 to the surrounding tissue can be enhanced by controlling the blood flow using expandable distal end portion 132.

In some embodiments, portions of the expandable distal end portion 132 can be enhanced to provide radiographic visualization of the position and orientation of the expandable distal end portion 132. For example, some embodiments include a loop of radiopaque material (e.g., titanium, tungsten, barium sulfate, zirconium oxide, and the like) around the mouth of the filter to allow for precise positioning and verification of apposition before proceeding with the intervention. Alternatively, or additionally, in some embodiments one or more radiopaque markers can be included on other portions of expandable distal end portion 132.

Figure 2A:
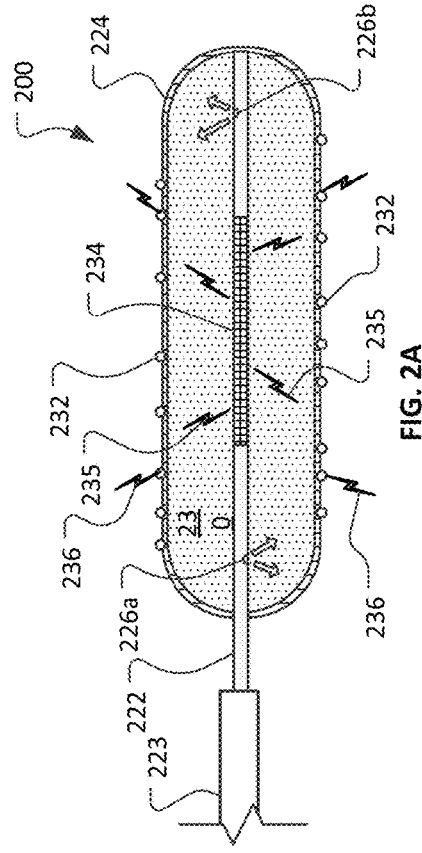
FIGS. 2A-2C are schematic illustrations of balloon catheters that are capable of simultaneously delivering ablation energy and a stenosis prevention agent in accordance with some embodiments provided herein.
Figure 2B:
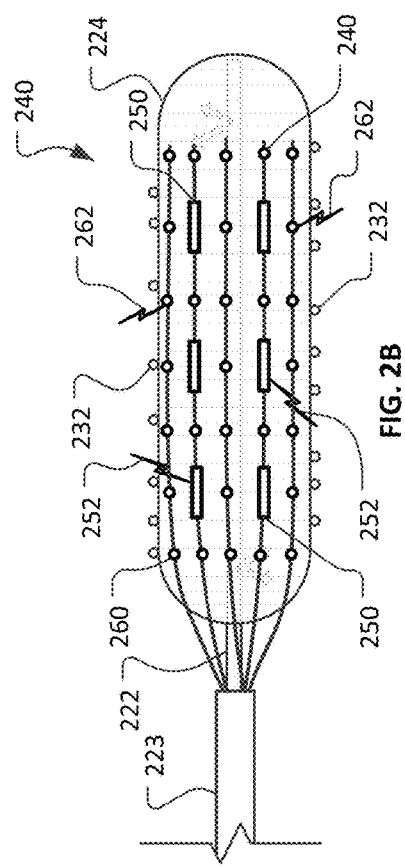
Figure 2C:
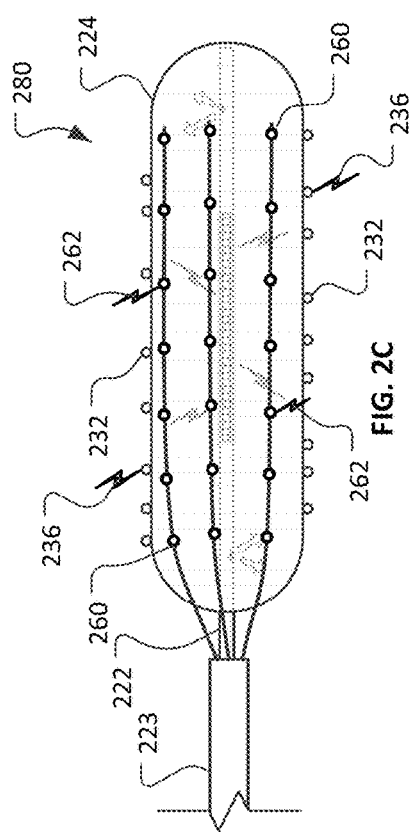

With reference to FIGS. 2A-2C, example embodiments of catheter-based balloon ablation devices 200, 240, and 280 are provided. These device embodiments are arranged to coordinate the delivery of tissue ablation energy and a liquid pharmacological agent to the tissue receiving the ablation energy. While the embodiments depicted are generally cylindrical, other shapes and a range of sizes are also envisioned to adapt the devices to the various applications described herein. It should be understood that other embodiments of catheter-based balloon ablation devices may be coated with a pharmacological agent. In some embodiments, a drug may be within a balloon (e.g., a drug embedded within the matrix of the balloon). In still other embodiments, the catheter-based balloon ablation devices provided herein may be used without the administration of any pharmacological agent that is administered directly by the balloon ablation device.

It should also be understood, that the features and usage techniques described herein in relation to the various ablation devices can be combined with the features of other ablation device embodiments and usage techniques described herein. Accordingly, based on such combinations and sub-combinations, an extensive number of ablation device embodiments and usage techniques are envisioned and provided herein.

FIG. 2A depicts a balloon catheter ablation device 200 that includes a catheter shaft 222 and a balloon device 224 that is disposed on the distal end of catheter shaft 222. Balloon device 224 is shown in an axial cross-sectional view to provide enhanced visualization of its interior space.

Balloon device 224 is shown in its inflated configuration, but balloon device 224 can be inflated and/or deflated as desired by a clinician operator. In general, during insertion and placement within a patient, balloon device 224 is in its deflated configuration. When deflated, balloon device 224 can be positioned within a low-profile delivery catheter 223. When the distal tip of delivery catheter 223 is located in a desired anatomical position within the patient, catheter shaft 222 can be moved distally in relation to delivery catheter 223 to make balloon device 224 emerge from the distal tip of delivery catheter 223. Balloon device 224 can then be inflated to make contact with the tissue of the patient, such as within a pulmonary vein (refer to FIG. 1).

An antimitotic pharmacological agent 230, such as paclitaxel, can be used as the inflation medium. Pharmacological agent 230 can be delivered from a source (not shown) located external to the patient, through a lumen in catheter shaft 222, and into the interior space of balloon device 224 through ports 226a-b located on catheter shaft 222 inside balloon device 224. In some embodiments, one inflation medium delivery port is included on catheter 222, but in other embodiments three or more ports are included. Pharmacological agent 230 can pressurize the interior space of balloon device 224 to cause balloon device 224 to inflate to the generally cylindrical configuration shown.

The material of balloon device 224 can be porous or microporous. As such, antimitotic pharmacological agent 230 can elute, exude, or weep from the interior of balloon device 224 to its exterior, as depicted by the multiple droplets 232. From the position on the exterior of balloon device 224, droplets 232 can contact the surrounding tissue (e.g., pulmonary vein 118 as shown in FIG. 1). The tissue can absorb droplets 232, which can prevent or reduce fibrosis, stenosis, and neointimal hyperplasia of the tissue.

Catheter shaft 222 can include an axial electrode 234 for the delivery of ablation energy. Electrode 234 can be electrically wired to an ablative energy source (not shown) located external to the patient. For example, in some embodiments an RF energy source can be used. In other embodiments, other types of energy can be used (e.g., DC, AC, cryogenic, microwave, laser, and the like). In some embodiments, a combination of such energy sources can be used within a single embodiment of ablation balloon device (e.g., RF and DC are used in combination is some embodiments). The ablation energy can be monopolar or bipolar.

In some embodiments, balloon catheter ablation device 200 can delivery ablation energy to surrounding tissue as follows. Electrical current can transfer from axial electrode 234 to pharmacological agent 230 as depicted by electrical symbols 235. In turn, electrical current can transfer from droplets 232 of pharmacological agent 230 to surrounding tissue as depicted by electrical symbols 236. In this fashion, delivery of ablation energy 236 and antimitotic pharmacological agent 230 can take place simultaneously from balloon ablation device 200 to surrounding tissue. In some cases, a layered delivery of ablation energy can be facilitated using the fluid to deliver the energy.

Using pharmacological agent 230 as an ablation/electroporation energy transfer mechanism can provide advantages in some situations. For example, in some cases multiphasic or single electrode delivery of ablation/electroporation energy via pharmacological agent 230 can allow for very low current dosage, but with very rapid frequency. Such multiphasic energy delivery or constant changing of bipolar vectors may serve to decrease the likelihood of induced ventricular arrhythmia as well as ventricular fibrillation in some cases.

With reference to FIG. 2B, an example balloon catheter ablation device 240 includes multiple electrodes 250 and 260 that are provided on the surface of balloon device 224. In some embodiments, electrodes 250 and 260 can be different types of electrodes, and/or electrodes 250 and 260 can be configured to deliver different types of energy. For example, in the embodiment of FIG. 2B electrodes 260 are DC electrodes and electrodes 250 are RF electrodes. DC electrodes 260 can provide DC electrical current 262, which can be well-suited to helping facilitate the uptake of droplets 232 of pharmacological agent 230 into surrounding tissue. RF electrodes 250 can provide RF energy 252, which can be well-suited to causing ablation and denervation of surrounding tissue.

The electrodes 250 and/or 260 can be individual electrodes (i.e., having individual contacts with a generator/controller device), segmented electrodes with two or more commonly connected contacts, or single continuous electrodes with a common contact. In some embodiments, the electrodes 250 and/or 260 may be configured to provide a bipolar signal. In some embodiments, electrodes 250 and/or 260 may be used, together or individually, in conjunction with a separate patient ground pad for monopolar use.

Balloon device 224 and catheter shaft 222 are described in reference to FIG. 2A. That is, balloon device 224 can provide antimitotic pharmacological agent 230 delivered from catheter shaft 222 to surrounding tissue in droplets 232. At the same time (if desired), or before or after delivery of the agent 230, electrodes 250 and 260 can be activated to provide energy 252 and 262 to surrounding tissue. In this fashion, delivery of ablation energy 252 and antimitotic pharmacological agent droplets 232 can take place in a coordinated fashion from balloon catheter ablation device 240 to surrounding tissue.

With reference to FIG. 2C, an example balloon catheter ablation device 280 includes DC electrodes 260 that are provided on the exterior surface of balloon device 224 and an RF axial electrode as described in reference to FIG. 2A. Balloon device 224 and catheter shaft 222 are also described in reference to FIG. 2A. Ablation energy 236 can be delivered to surrounding tissue from the internal RF axial electrode via the droplets 232 of antimitotic pharmacological agent 230. DC energy can be provided from surface electrodes 260 to help facilitate the uptake of droplets 232 of pharmacological agent 230 into surrounding tissue. In this fashion, delivery of ablation energy 236 and antimitotic pharmacological agent droplets 232 can take place simultaneously or in a sequentially coordinated manner from balloon ablation device 280 to surrounding tissue.

Figure 2D:
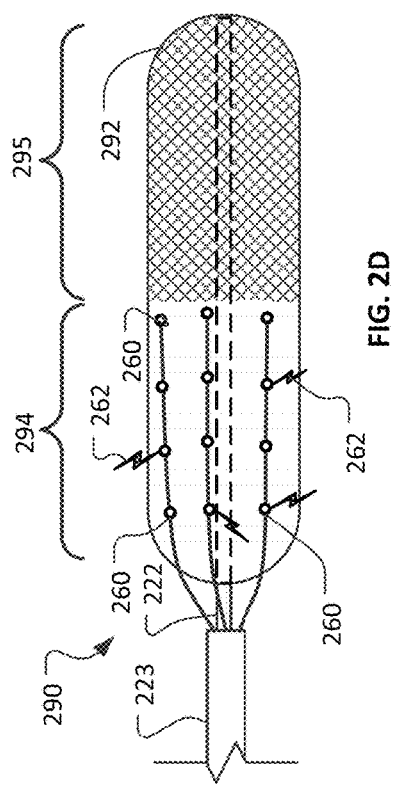
FIG. 2D is a schematic illustration of a balloon catheter with ablation electrodes on a first portion of the balloon and a drug coating on a second portion of the balloon.

With reference to FIG. 2D, an example of another embodiment of a balloon catheter ablation device 290 includes an ablation portion 294 and an antimitotic pharmacological agent delivery portion 295 on a single balloon device 292. In this embodiment, ablation portion 294 is located proximally of antimitotic pharmacological agent delivery portion 295. In alternative embodiments, ablation portion 294 can be located distally of antimitotic pharmacological agent delivery portion 295. In some embodiments, antimitotic pharmacological agent delivery portion 295 is a drug-coated portion of balloon device 292. In other embodiments, balloon device 292 can be partly or fully made from a porous or microporous material, and an antimitotic pharmacological agent can be supplied as an inflation fluid such that the pharmacological agent can elute, weep, or be otherwise transmitted through balloon device 292 to the tissue.

In one example implementation of balloon catheter ablation device 290, ablation portion 294 is first positioned adjacent to the target tissue. Catheter shaft 222 can be used to move balloon device 292 proximally and distally as desired. Balloon device 292 can then be inflated with an inflation fluid such that electrodes 260 make contact with the tissue. Ablation energy 262 can then be provided from electrodes 260 to the tissue. After delivery of ablation energy 262 as desired, the inflation fluid can be at least partially removed from balloon device 292 to reduce the outer diametrical size of balloon device 292. Using catheter shaft 222, balloon device 292 can then be retracted proximally so that antimitotic pharmacological agent delivery portion 295 is approximately in position to make contact with the tissue that received ablation energy 262. Then inflation fluid can again be supplied to balloon device 292 such that the surface of antimitotic pharmacological agent delivery portion 295 makes contact with the ablated tissue. The antimitotic pharmacological agent can thereby be transferred to the tissue. That is, in embodiments that have an antimitotic pharmacological agent coated on the surface of antimitotic pharmacological agent delivery portion 295, the contact between the coating and the tissue can facilitate transfer of the pharmacological agent to the tissue. In other embodiments, balloon device 292 can be partly or fully made from a porous or microporous material, and the antimitotic pharmacological agent can elute, weep, or be otherwise transmitted through balloon device 292 to the tissue.

Figure 3A:
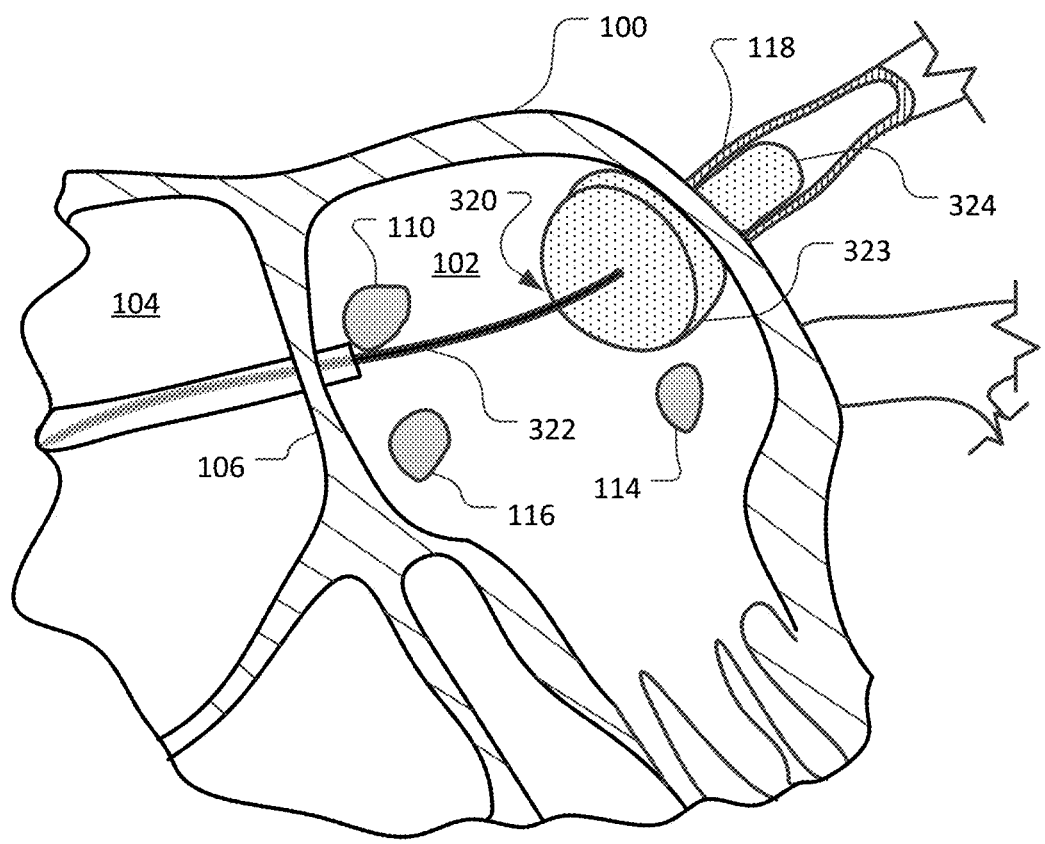
FIG. 3A is a schematic diagram of heart undergoing a pulmonary vein ablation using another catheter-based device in accordance with some embodiments provided herein.

With reference to FIG. 3A, heart 100 is depicted as receiving an ablation procedure using an example balloon catheter ablation device 320. Balloon catheter ablation device 320 is similar to other balloon catheter ablation devices described herein but with the addition of a bulbous proximal balloon portion 323 that contacts and delivers ablation energy to the tissue surrounding the ostium of pulmonary vein 118.

In some embodiments, bulbous proximal balloon portion 323 can include electrodes that function as return electrodes for ablation/electroporation energy delivered by more distally-located electrodes or by charge-carrying solution (e.g., a pharmacological agent, saline, heparinized-saline, etc.) that is distally-positioned on/by balloon catheter ablation device 320. Such an arrangement can serve to limit the bipolar field in some circumstances. The polarity can be reverse, also. Moreover, in some embodiments, multiphasic energy delivery concepts can be applied in the context of electrodes on bulbous proximal balloon portion 323 in comparison to electrodes that are more distally located.

Figure 3B:
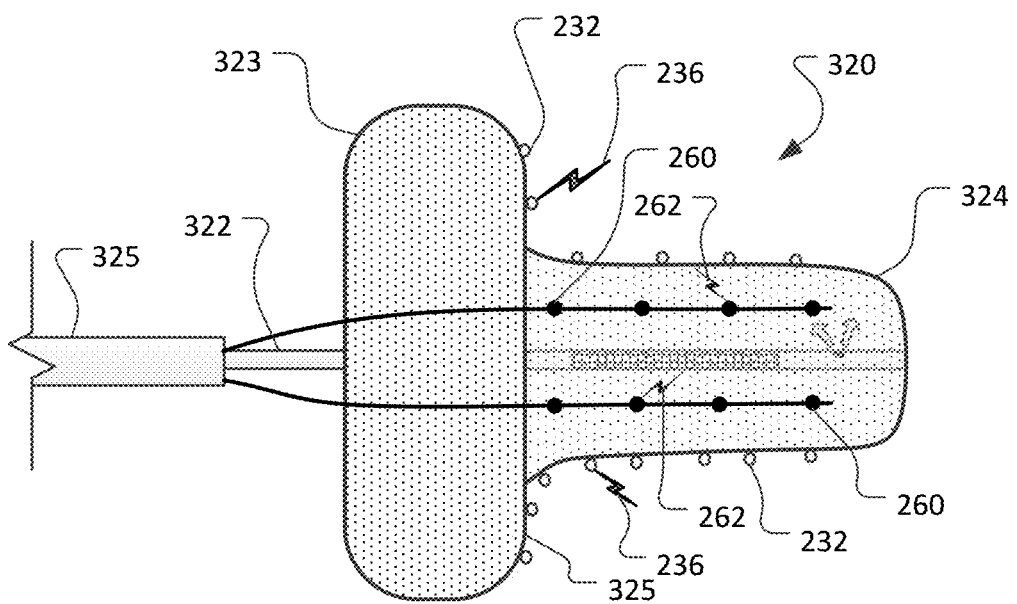
FIG. 3B is a schematic illustration of another balloon catheter that is capable of simultaneously delivering ablation energy and a stenosis prevention agent in accordance with some embodiments provided herein.

FIG. 3B illustrates balloon catheter ablation device 320, including its distal generally cylindrical balloon portion 324 in addition to bulbous proximal balloon portion 323. In some embodiments, the balloon portions 323 and 324 are in fluid communication with each other to provide a single balloon interior space. In alternate embodiments, the balloon portions 323 and 324 have separated volumetric spaces that are each supplied with inflation fluid from individually discrete lumens in catheter shaft 322. In still other embodiments, a single lumen supplies both balloon portions 323 and 324, but as inflation fluid is supplied, cylindrical balloon portion 324 inflates first and bulbous proximal balloon portion 323 inflates after the time at which cylindrical balloon portion 324 is substantially inflated or nearly substantially inflated.

A liquid antimitotic pharmacological agent can be delivered via catheter shaft 322 to inflate balloon portions 323 and 324. Pharmacological agent droplets 232 can form on the exterior surfaces of either or both of balloon portions 323 and 324 that are in contact with surrounding tissue. Electrodes 260 can deliver DC energy 262 to help facilitate uptake of pharmacological agent droplets 232 by surrounding tissue.

Ablation energy can be delivered in various ways. In some embodiments, a central axial electrode is included on catheter shaft 322 to electrify the droplets 232 as depicted by electrical symbols 236. In some embodiments, surface electrodes (e.g., RF electrodes) can be located on the surface of balloon portions 323 and/or 324. In some embodiments, such surface electrodes can be located on the distal face 325 of bulbous proximal balloon portion 323 that contacts the myocardial tissue at the circumferential margin of pulmonary vein ostia. In some embodiments, a combination of types and locations of electrodes can be used on balloon catheter ablation device 320. Energy can be delivered simultaneously or sequentially with the delivery of pharmacological agent, if so desired. In this fashion, delivery of ablation energy and antimitotic pharmacological agent droplets 232 can take place in a temporally coordinated manner from balloon catheter ablation device 320 to surrounding tissue.

Figure 4A:
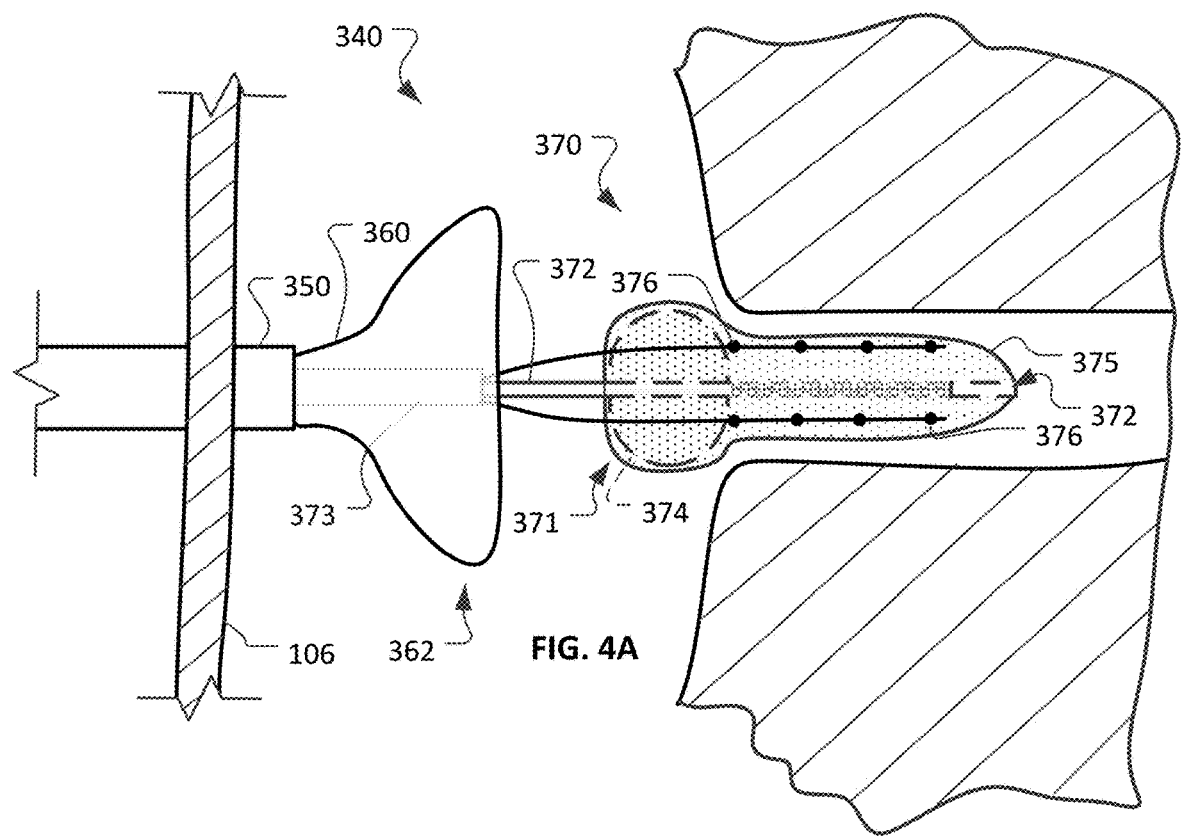
FIG. 4A is a schematic illustration of another a partially deployed system for pulmonary vein ablation in accordance with some embodiments provided herein.
Figure 4B:
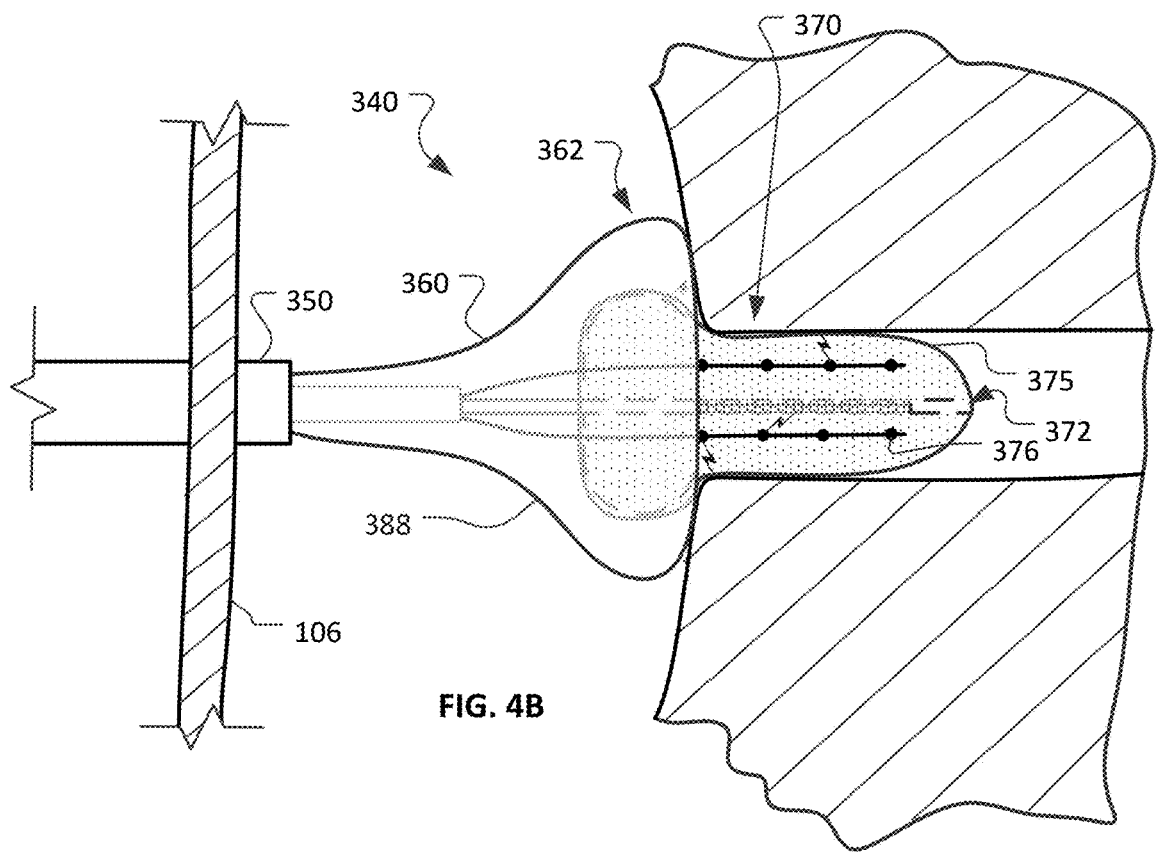
FIG. 4B is the schematic diagram of FIG. 4A with the system for pulmonary vein ablation fully deployed such that ablation and particulate capture can take place.

FIGS. 4A and 4B illustrate another embodiment of a catheter-based ablation system 340 in accordance with some embodiments provided herein. Catheter-based ablation system 340 includes a transseptal sheath 350, a hood catheter 360, and a balloon catheter ablation device 370. Hood catheter 360 is slidably disposed within a lumen of transseptal sheath 350. Balloon catheter ablation device 370 is slidably disposed within a lumen of hood catheter 360.

In some embodiments, hood catheter 360 is contained within transseptal sheath 350 in a collapsed low-profile delivery configuration during navigation of balloon catheter ablation device 370 to the target site, and balloon catheter ablation device 370 in a collapsed low-profile delivery configuration is within a lumen of hood catheter 360. At the target site, hood catheter 360 can be deployed, that is, made to emerge from transseptal sheath 350. Hood catheter 360 may be deployed before the deployment of balloon catheter ablation device 370 in some embodiments. However, in some embodiments, hood catheter 360 may be deployed after the deployment of balloon catheter ablation device 370. In still other embodiments, hood catheter 360 may be deployed essentially simultaneously with balloon catheter ablation device 370.

In the depiction of FIG. 4A, balloon catheter ablation device 370 is deflated, and hood catheter 360 is expanded but not in position to capture particulate. In the depiction of FIG. 4B, balloon catheter ablation device 370 is inflated, and hood catheter 360 is expanded and in position to capture particulate.

Hood catheter 360 is configured to be collapsed into a low-profile delivery configuration for containment within transseptal sheath 350. In addition, an expandable distal end portion 362 of hood catheter 360 is configured to expand (as shown) to a radially expanded configuration. In some embodiments, expandable distal end portion 362 is self-expandable and is biased to expand to the radially expanded configuration upon emergence from transseptal sheath 350. In some embodiments, expandable distal end portion 362 is selectively deployable by a proximally-located ex vivo deployment actuator.

As expandable distal end portion 362 deploys, it radially expands into a generally conical or frustoconical shape, such that an enlarged interior space is defined within expandable distal end portion 362. In some embodiments, expandable distal end portion 362 is expanded using mechanisms and techniques such as, but not limited to, inflation, shape-set materials (e.g., a nitinol frame), one or more control wires, mechanical linkages, and the like, and combinations thereof. In some embodiments, expandable distal end portion 362 may include one or more pleats, folds, elastic portions, and the like. Expandable distal end portion 362 can be constructed of any of the materials described in reference to expandable distal end portion 132 and can optionally include any of the features described in reference to expandable distal end portion 132.

After the deployment of expandable distal end portion 362, hood catheter 360 can be advanced to enclose the area to be treated by balloon catheter ablation device 370 (as depicted in FIG. 4B). Hood catheter 360 is configured to maintain full-wall apposition against the topography defined by the tissue wall.

Balloon catheter ablation device 370 includes a bulbous proximal portion 371 and a generally cylindrical distal balloon portion 372. In this example implementation, balloon catheter ablation device 370 is depicted as making contact with tissue surrounding the ostium of a pulmonary vein, and projecting into the pulmonary vein. It should be understood that other types of ablation devices, and ablation procedures at other areas of the heart, can be performed using the devices and techniques provided herein without departing from the scope of the disclosure.

In this embodiment, the bulbous proximal shape is achieved by having an internal balloon 374 (shown in dashed lines) inside of an outer balloon 375. Internal balloon 374 has an inflated diameter that is larger than the diameter of the inflated generally cylindrical distal portion of outer balloon 375. Each of the balloons 374 and 375 is supplied with inflation media via an individually discrete lumen. That is, central catheter 372 has a first lumen that is in fluid communication with the inner balloon 374 and a separate second lumen that is fluid communication with the outer balloon 375.

In some implementations of balloon catheter ablation device 370, inner balloon 374 is inflated with a gas such as air or carbon dioxide. Outer balloon 375, in contrast, can be inflated with a pharmacological agent that can, in some embodiments, be eluted through a porous or microporous material of outer balloon 375 to thereby make contact with the tissue of the pulmonary vein or renal artery to provide a therapeutic effect. For example in some embodiments the exudation and elution of a liquid pharmacological agent can serve to the prevent or reduce vessel stenosis and neointimal hyperplasia. For instance, the drug paclitaxel is an example of one type of an antimitotic pharmacological agent that can be delivered to the tissue undergoing ablation to prevent or reduce fibrosis and stenosis of the tissue. Paclitaxel can be used beneficially because of its rapid uptake and prolonged retention. In some implementations, paclitaxel can be delivered in 3% saline (or similar hypertonic solution) to further enhance its uptake and retention. While paclitaxel is provided as an example, other pharmacological agents can also be used.

In some embodiments, the pharmacological agent can transmit ablation energy as described in reference to, for example, balloon ablation device 200 of FIG. 2A. At the same time (if desired), or before or after delivery of the pharmacological agent, surface electrodes 376 can be activated to provide ablation energy to surrounding tissue. In this fashion, delivery of ablation energy and antimitotic pharmacological agent can take place in a coordinated fashion from balloon catheter ablation device 370 to surrounding tissue including the ostium of a pulmonary vein or renal vein, and projecting into the pulmonary vein or renal vein. Such methods may further comprise energizing one or more electrodes for enhancing an uptake of the pharmacological agent by the tissue.

In some implementations, prior to deflation of balloon catheter ablation device 370, the blood within the space between expandable distal end portion 362 and the tissue wall is suctioned out (e.g., vacuum aspirated). Such suction can be used to ensure that any particulate that may be present in the blood within the space between expandable distal end portion 362 and the tissue wall is removed from the patient's vasculature. In some implementations, after the initial suctioning, a rinse solution (e.g., saline) may be supplied into the space between expandable distal end portion 362 and the tissue wall, and thereafter suctioned out. Using such a rinse solution and procedure may serve to remove additional potential emboli. In some cases, the rinse procedure may be used a single time, or may be repeated two, three, four, or more than four times.

After the aspiration of particulate, balloon catheter ablation device 370 may be deflated and withdrawn into hood catheter 360. Expandable distal end portion 362 can be collapsed into a low-profile configuration. Then, hood catheter 360 and balloon catheter ablation device 370 can be withdrawn into transseptal sheath 350. Thereafter, catheter-based ablation system 340 can be withdrawn from the patient.

In some embodiments, the pore size of expandable distal end portion 362 can be selected as desired to provide the desired embolic protection while allowing the transmission of blood flow therethrough. For example, in some embodiments expandable distal end portion 132 may have a pore size in the range of about 40 μm to about 60 μm, about 50 μm to about 70 μm, about 60 μm to about 80 μm, about 70 μm to about 90 μm, about 80 μm to about 100 μm, about 90 μm to about 110 μm, about 100 μm to about 120 μm, about 110 μm to about 130 μm, about 120 μm to about 140 μm, about 130 μm to about 150 μm, about 140 μm to about 160 μm, or greater than 160 μm.

In some such embodiments, the pore size of expandable distal end portion 132 can be selected so that expandable distal end portion 132 will occlude all or substantially all blood flow therethrough. In this manner, particulate can be captured within the space between expandable distal end portion 362 and the tissue wall. Moreover, in this manner blood flowing between outer balloon 375 and the tissue with which outer balloon 375 makes contact can be reduced or eliminated as desired. Similarly, blood flowing in the space between expandable distal end portion 362 and the tissue wall with which it makes contact can be reduced or eliminated as desired. By so controlling the blood flow using expandable distal end portion 362, the therapeutic efficacy of balloon catheter ablation device 370 can be enhanced in some circumstances. For example, in some circumstances the uptake of liquid pharmacological agents and/or the transfer of ablation energy from balloon catheter ablation device 370 to the surrounding tissue can be enhanced by controlling the blood flow using expandable distal end portion 362.

In some embodiments, portions of hood catheter 360 can be enhanced to provide radiographic visualization of the position and orientation of the hood catheter 360. For example, some embodiments include a loop of radiopaque material (e.g., titanium, tungsten, barium sulfate, zirconium oxide, and the like) around the mouth of the filter to allow for precise positioning and verification of apposition before proceeding with the intervention. Alternatively, or additionally, in some embodiments one or more radiopaque markers can be included on other portions of hood catheter 360.

Figure 5:
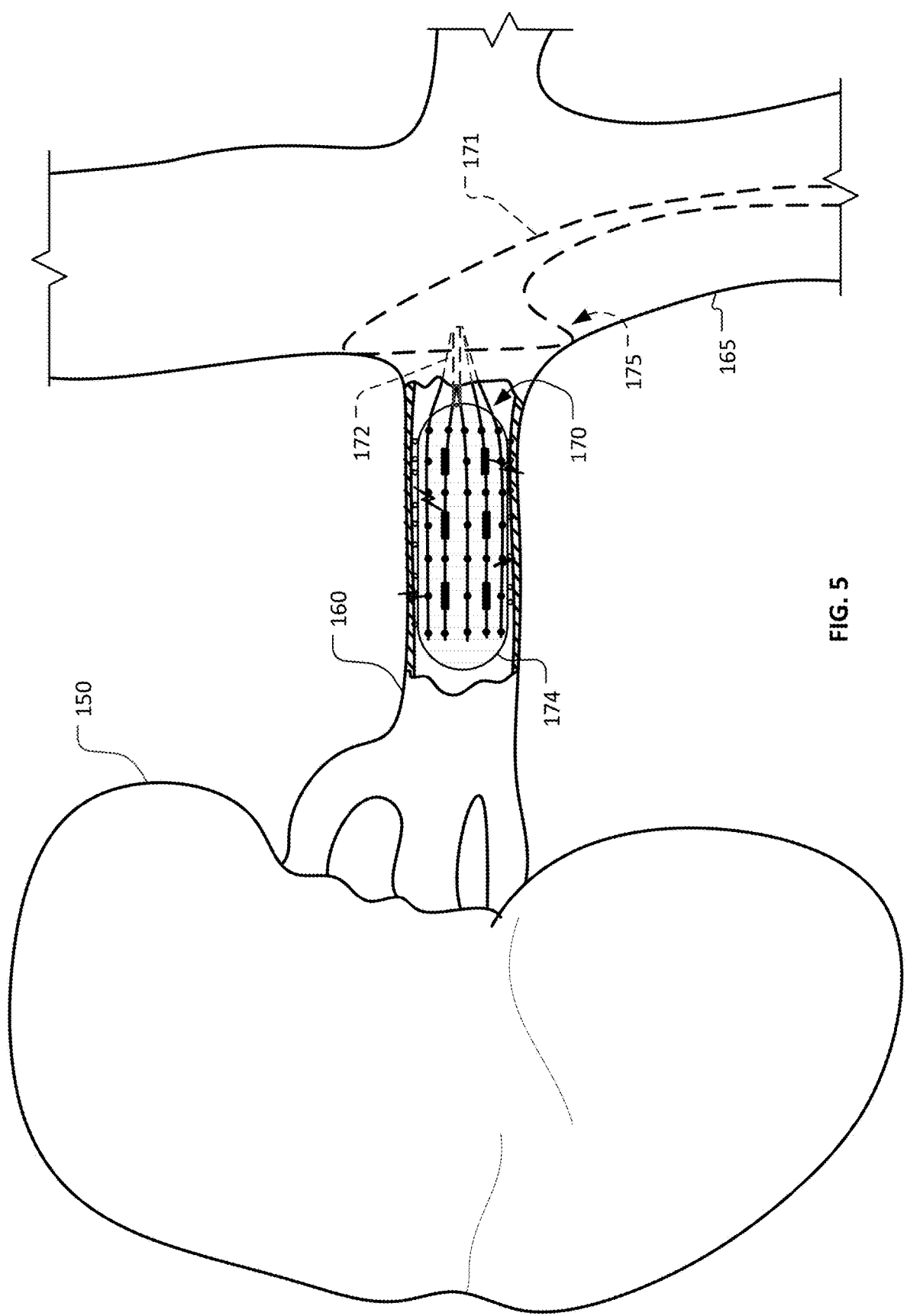
FIG. 5 is a schematic diagram of renal artery undergoing an ablation procedure using a catheter-based ablation and emboli capture system in accordance with some embodiments provided herein.

FIG. 5 is a schematic diagram of a kidney 150 and a renal artery 160 undergoing an ablation procedure using a example balloon catheter ablation device 170 in accordance with some embodiments provided herein. In some cases, this technology may allow for a complete and full length ablation of renal artery 160 without fear of causing stenosis or emboli, both at the ostia, distal, and middle segments.

In the depicted implementation, the balloon catheter ablation device 170 was directed to the site of the renal artery 160 via the femoral artery and the aorta 165 using a delivery sheath 171 that includes an expandable distal end portion 175. However, other approaches may also be used. In general, balloon catheter ablation device 170 includes a multi-lumen catheter shaft 172 that is coupled to a balloon device 174. The proximal end of balloon catheter ablation device 170 is connected to an ablation energy source and controller (e.g., an RF generator system, not shown) and a liquid pharmacological agent source (not shown), both of which are located external to the patient.

Balloon device 174 is located at the distal end of catheter shaft 172. An interior space of balloon device 174 is in fluid communication with a liquid delivery lumen of catheter shaft 172. In this embodiment, the liquid delivery lumen is used to convey the liquid pharmacological agent from the source external to the patient into the interior space of balloon device 174. In alternative embodiments, the balloon device 174 can be coated with a pharmacological agent. In still other embodiments, no pharmacological agent is so used.

In some embodiments, balloon device 174 is designed to allow blood flow for perfusion while balloon device 174 is in its expanded (inflated) configuration. In some such embodiments, balloon device 174 has one or more channels in the outer profile of balloon device 174. The one or more channels provide open flow paths for blood, while other portions of the outer periphery of balloon device 174 are in contact with the inner wall of the vessel/structure (e.g., renal artery 160) to provide electroporation/ablation thereto. Such a balloon device configuration is also used, in some implementations, in vessels such as, but not limited to, carotid artery, and other central and peripheral arteries. For example, in the carotid or peripheral artery and the proximal aorta and coronary arteries, the balloon continues perfusion and concurrent electroporation without heating or thermal effect to treat the arterial wall for a variety of arterial wall pathology including atheroma.

With balloon catheter ablation device 170 positioned within renal artery 160, in some embodiments balloon device 174 can be inflated using a liquid pharmacological agent as the inflation medium. In alternative embodiments, other inflation media can be used such as, but not limited to, saline, air, or carbon dioxide. The inflation of balloon device 174 will cause the outer surface of balloon device 174 to make contact with the inner wall of renal artery 160. In addition, in embodiments so configured, the pressure of the liquid pharmacological agent inflation medium will cause some of the pharmacological agent to exude, elute, weep, or otherwise be transmitted from within the interior space of the balloon 174 to the exterior surface of the balloon 174, and into contact with the inner wall of renal artery 160. At this juncture, (or before, or during such transmission, or using a combination of such techniques) balloon catheter ablation device 170 can be energized with ablation energy to initiate the modulation and denervation of target neural fibers.

In another type of implementation for renal artery 160, we can place balloon catheter ablation device 170 in the renal vein and can perform bipolar electroporation with a first balloon in the renal vein and a second balloon in the renal artery. In addition, in some embodiments the renal vessel is purposely dilated using the balloon device so as to increase the antenna or range of the electrodes for both bipolar and monopolar ablation.

In some embodiments, the ablation process of renal artery 160 can be performed simultaneously and concurrently with the delivery of an antimitotic pharmacological agent to the tissue receiving the ablation energy. Alternatively, the ablation process can be performed sequentially with the delivery of an antimitotic pharmacological agent to the tissue receiving the ablation energy. That is, the antimitotic pharmacological agent can be delivered first and the ablation process can take place thereafter. Or, the antimitotic pharmacological agent can be delivered after the ablation process. In some implementations, a combination of such techniques can be used. For example, the antimitotic pharmacological agent can be delivered before and during the ablation process, or before and after, and so on. In other embodiments, balloon 174 is coated with a pharmacological agent that is absorbed into the tissue of renal artery 160. In still other procedures, no pharmacological agent is administered using balloon catheter ablation device 170.

In some implementations, prior to deflation of balloon 174, the blood within the space between expandable distal end portion 175 and the tissue wall is suctioned out (e.g., vacuum aspirated). Such suction can be used to ensure that any particulate that may be present in the blood within the space between expandable distal end portion 175 and the tissue wall is removed from the patient's vasculature. In some implementations, after the initial suctioning, a rinse solution (e.g., saline) may be supplied into the space between expandable distal end portion 175 and the tissue wall, and thereafter suctioned out. Using such a rinse solution and procedure may serve to remove additional potential emboli. In some cases, the rinse procedure may be used a single time, or may be repeated two, three, four, or more than four times.

After the aspiration of particulate, balloon catheter ablation device 170 may be deflated and withdrawn into delivery sheath 171. Expandable distal end portion 175 can be collapsed into a low-profile configuration. Thereafter, delivery sheath 171 containing balloon catheter ablation device 170 can be withdrawn from the patient.

Figure 6:
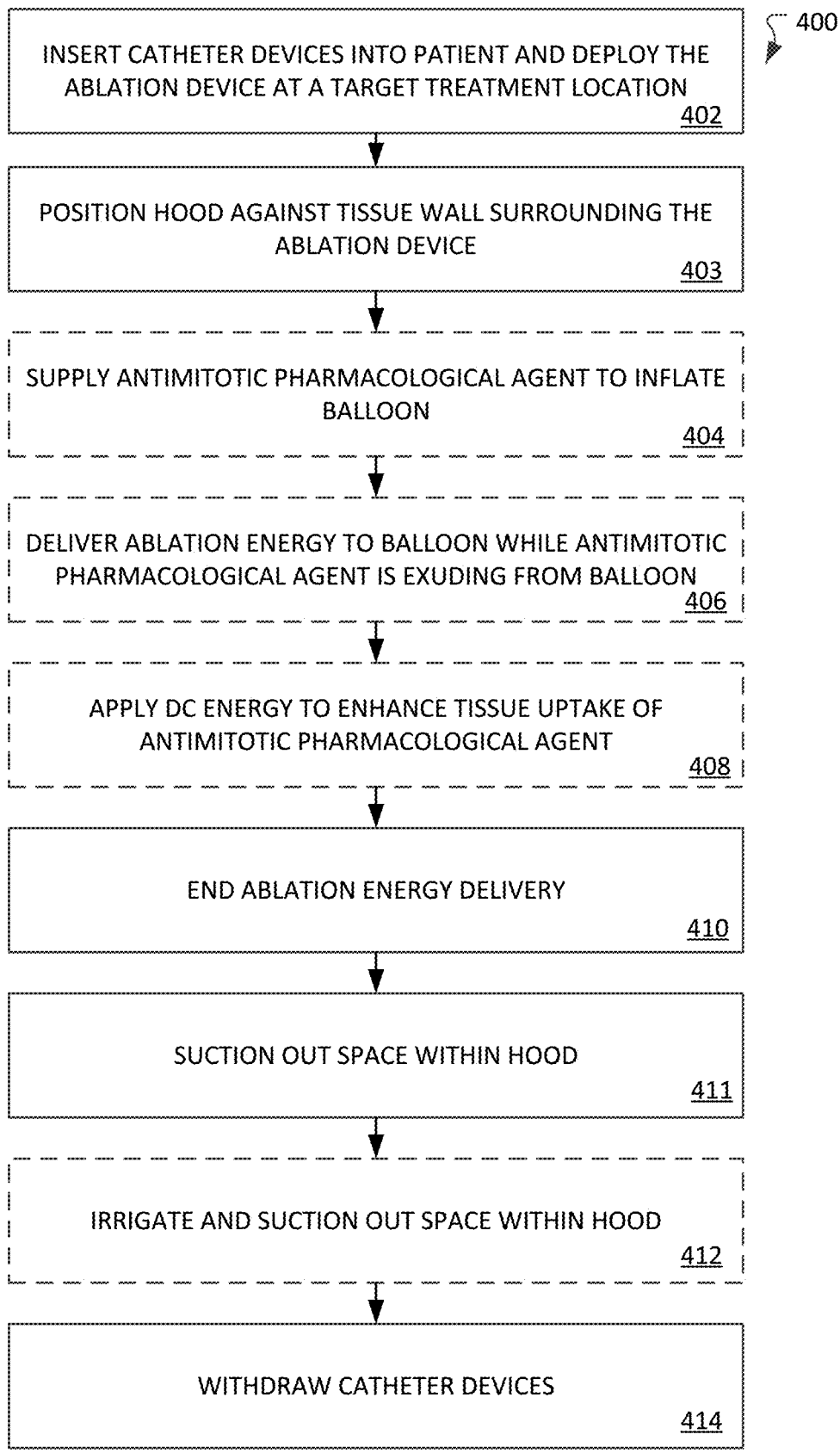
FIG. 6 is flowchart of an exemplary ablation method in accordance with some embodiments provided herein.

With reference to FIG. 6, a flowchart of a process 400 for ablating a target tissue while optionally simultaneously delivering an antimitotic pharmacological agent to prevent or reduce stenosis of the tissue, and capturing and removing particulate (e.g., thrombus, drug particulate, etc.), is provided. While process 400 is described as using a catheter-based balloon ablation device (such as those described herein) it should be understood that other types of ablation devices can be used for process 400 (with or without the capability to simultaneously deliver an antimitotic pharmacological agent).

At operation 402, one or more catheter devices are inserted into a patient by a clinician. In some cases, a guidewire is inserted first and the catheter(s) is inserted over or on the guidewire. The catheter can be a delivery catheter or sheath that contains an ablation catheter with a distally located balloon device in a deflated state. In some embodiments, the delivery catheter has an expandable distal end portion or hood (e.g., like introducer sheath 130 described herein). In some embodiments, the delivery catheter contains a hood catheter that has an expandable distal end portion (e.g., like hood catheter 360 described herein), and the ablation device is within the hood catheter.

When the ablation device is a balloon device, in some embodiments the balloon device can be porous or microporous such that a liquid can be made to exude, elute, or weep out from the balloon device as described herein. The balloon catheter can also include one or more electrodes for the delivery of energy to the patient's tissue. The delivery catheter and/or the balloon catheter can include one or more radiopaque markers to assist with radiographically visualizing the positioning of the catheters within the patient. The catheters can be routed within the patient to a position where the distal end of the delivery catheter is near the target treatment location (e.g., a pulmonary vein as described in reference to FIGS. 1A-1C, or other treatment locations as desired). The clinician can cause the balloon device to emerge from the delivery catheter(s) into a desired position at the target treatment site.

At operation 403, a hood of a catheter is positioned against the tissue wall surrounding the ablation device. The hood is an expandable distal end portion of a catheter such as a delivery sheath (e.g., like introducer sheath 130 described herein) or an additional catheter (e.g., like hood catheter 360 described herein) contained within a delivery sheath. By positioning the expandable hood against the tissue wall surrounding the ablation device, a space is defined therein in which particulate matter can be captured and later removed (e.g., suctioned out).

At operation 404, the clinician can optionally supply an antimitotic pharmacological agent solution through a lumen of the balloon catheter to infill the balloon device at the distal end of the balloon catheter. The delivery of the solution will cause the balloon device to inflate and make contact with surrounding tissue. Pressurizing the balloon device with the antimitotic pharmacological agent can also cause some of the antimitotic pharmacological agent to exude, elute, or weep from the balloon device to the surrounding tissue. The antimitotic pharmacological agent can prevent or reduce fibrosis and stenosis of the tissue. In other embodiments, as an alternative to using the antimitotic pharmacological agent solution to infill the balloon device, the balloon device can be drug-coated and a different type of inflation fluid can be used (e.g. saline). In still other embodiments, the balloon device can be drug-coated and an antimitotic pharmacological agent solution can be used to infill the balloon device. In still other embodiments, no pharmacological agent is administered directly from the balloon device.

At operation 406, the clinician can optionally cause ablation energy to be delivered to the one or more electrodes at the balloon ablation device. This operation can optionally be temporally coordinated before, concurrently, and/or after the exuding of the antimitotic pharmacological agent in operation 404 as desired. The ablation energy can cause ablation or denervation of the tissue at the target treatment location. At the same time, the antimitotic pharmacological agent delivered to the tissue can prevent or reduce the occurrence of stenosis of the tissue receiving the ablation.

At operation 408, the clinician can optionally cause DC energy to be supplied to one or more electrodes on the balloon device. The provision of such energy can assist with the uptake of the antimitotic pharmacological agent into the tissue.

At operation 410, the ablation energy is discontinued. In some cases, the effects of the process operations above can be monitored and repeated as necessary, or the catheters can be repositioned to treat another target treatment location within the patient.

At operation 411, the space within the hood is suctioned out to remove particulate that may be located within the space. In some cases, the ablation process may result in the formation of some particulate matter such as, but not limited to, thrombi or crystalline drug compounds. The hood (with its distal end compressed against the tissue wall such that the ablation device is located within the space defined by the hood) can contain such particulate matter. By suctioning out the space within the hood, the potentially harmful emboli (particulate matter) can be removed from the patient's vasculature. To perform such suctioning (also referred to herein as "aspiration"), in some implementations a vacuum source is connected to a proximal end of the catheter that has the hooded distal end portion. The blood that potentially contains particulate can thereby be suctioned out of the patient's vasculature, preventing the particulate from becoming emboli.

At operation 412, the space within the hood can be optionally flushed by irrigating it and re-aspirating it. This optional operation can remove additional particulate matter in some cases. In some implementations, saline is the irrigant added into the space within the hood to flush out additional particulate. After the addition of the irrigant, suction can be applied to aspirate the irrigant and particulate matter contained in the irrigate. In some cases, two or more irrigation and re-aspiration steps are performed.

At operation 414, the catheters are withdrawn from the patient to conclude the treatment process 400. If the ablation device is a balloon ablation device, first the balloon can be deflated. Then the balloon ablation device can be withdrawn into the hood catheter or sheath. Then the hood can be collapsed to a low profile configuration. Then the entire catheter-based ablation system can be withdrawn from the patient.

Figure 7:
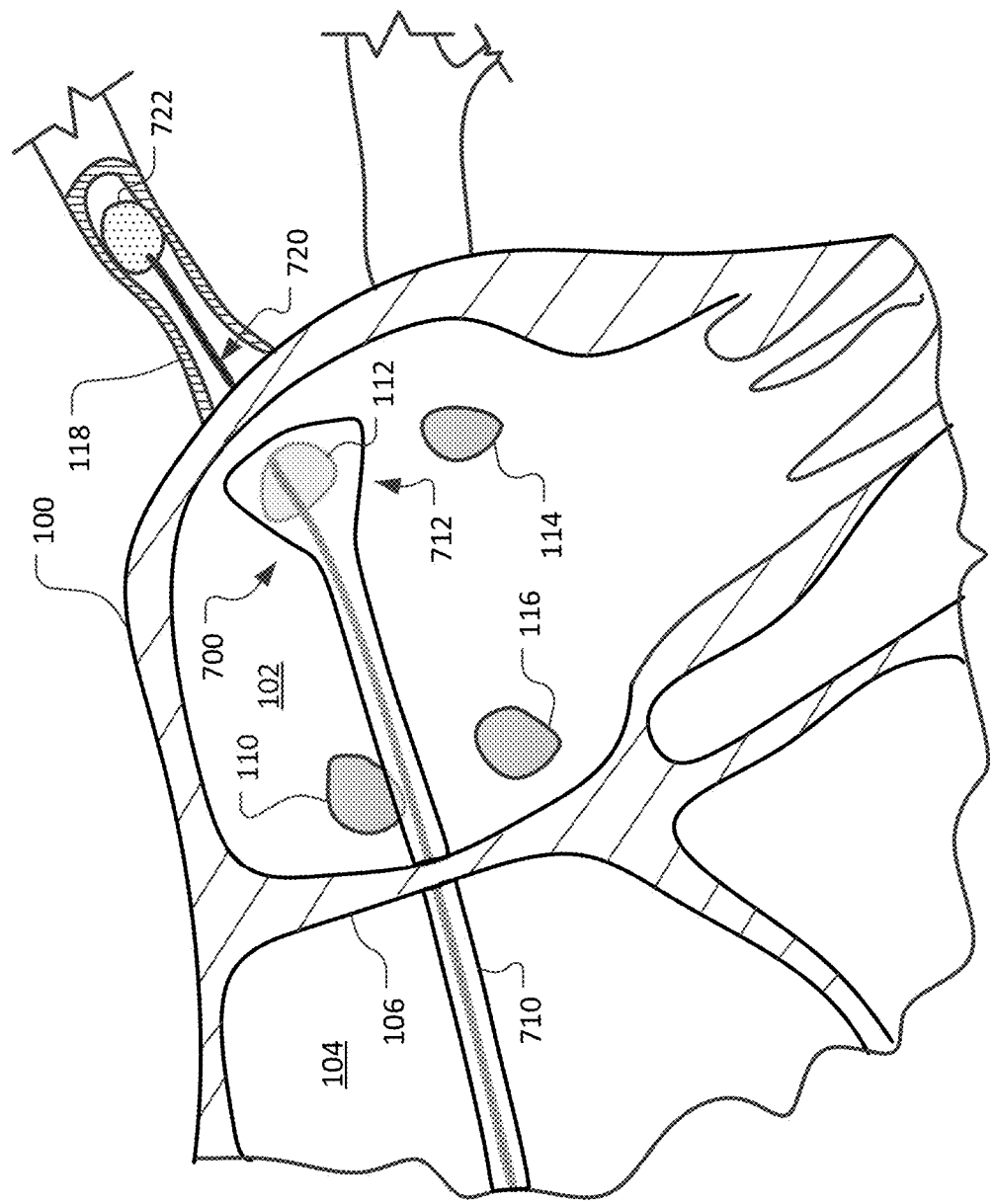
FIG. 7 is a schematic diagram of a catheter-based system for suctioning cells to cause cell death.

Referring to FIG. 7, a catheter-based system 700 can, in some implementations, be used to apply suction to a vessel to cause death of cells of the vessel. Catheter based-system 700 includes a hood catheter 710 and a balloon catheter 720. Balloon catheter 720 is slidably disposed within a lumen of hood catheter 710. In some embodiments, a delivery sheath is included, in which hood catheter 710 is slidably disposed.

While the depicted implementation is for treating a pulmonary vein 118, it should be understood that the devices and techniques can be similarly applied in the context of other vessels such as, but not limited to, an aorta, a coronary artery, the superior vena cava, and the like (e.g., as described elsewhere herein).

Hood catheter 710 includes an expandable distal end portion 712. Hood catheter 710 can be used to apply suction to pulmonary vein 118. In some embodiments, hood catheter 710 can be configured like hood catheter 360 and/or transseptal introducer sheath 130 as described herein. In use, expandable distal end portion 712 can be radially expanded and positioned into full-wall apposition with the tissue wall of atrium 102. A fluid seal is achieved around the periphery of the expandable distal end portion 712 against the tissue wall.

Balloon catheter 720 includes a distal balloon 722. Distal balloon 722 can be inflated to seal pulmonary vein 118. Hence, with distal balloon 722 inflated at a distal location within pulmonary vein 118, and hood catheter in full-wall apposition with the tissue wall of atrium 102, a portion of pulmonary vein 118 is fluidically isolated. Suction can then be applied via hood catheter 710. Such suction will cause pulmonary vein 118 to collapse to a smaller than natural diameter.

It has been found that by suctioning to collapse vessels to a smaller than natural diameter (e.g., as described here in the context of catheter-based system 700) cell death occurs. In other words, such a treatment provides a non-thermal method of causing cell death. Suctioning treatments porates the cell membranes and causes irreversible cell death. In some implementations, enough suction may be applied to completely collapse the vessel.

In some implementations, electroporation within the space between the expandable distal end portion 712 and the distal balloon 722 is also optionally applied.

Alternatively, in some embodiments, rather than using a hood catheter, a proximal balloon (not shown) can be included as a part of balloon catheter 720. The proximal balloon and distal balloon 722 are spaced apart such that a vessel chamber is defined therebetween when the catheter 720 is deployed in a vessel. Balloon catheter 720 can also have a lumen by which suction is applied within the chamber to collapse or partially collapse the vessel portion between the balloons.

In another implementation using catheter-based system 700, distal balloon 722 acts as an electrode placed well within the circulation region of interest. A fluid can be filled into the chamber defined between distal balloon 722 and hood catheter 710. The fluid can act as a virtual electrode for delivering ablation/electroporation energy to pulmonary vein 118.

Figure 8:
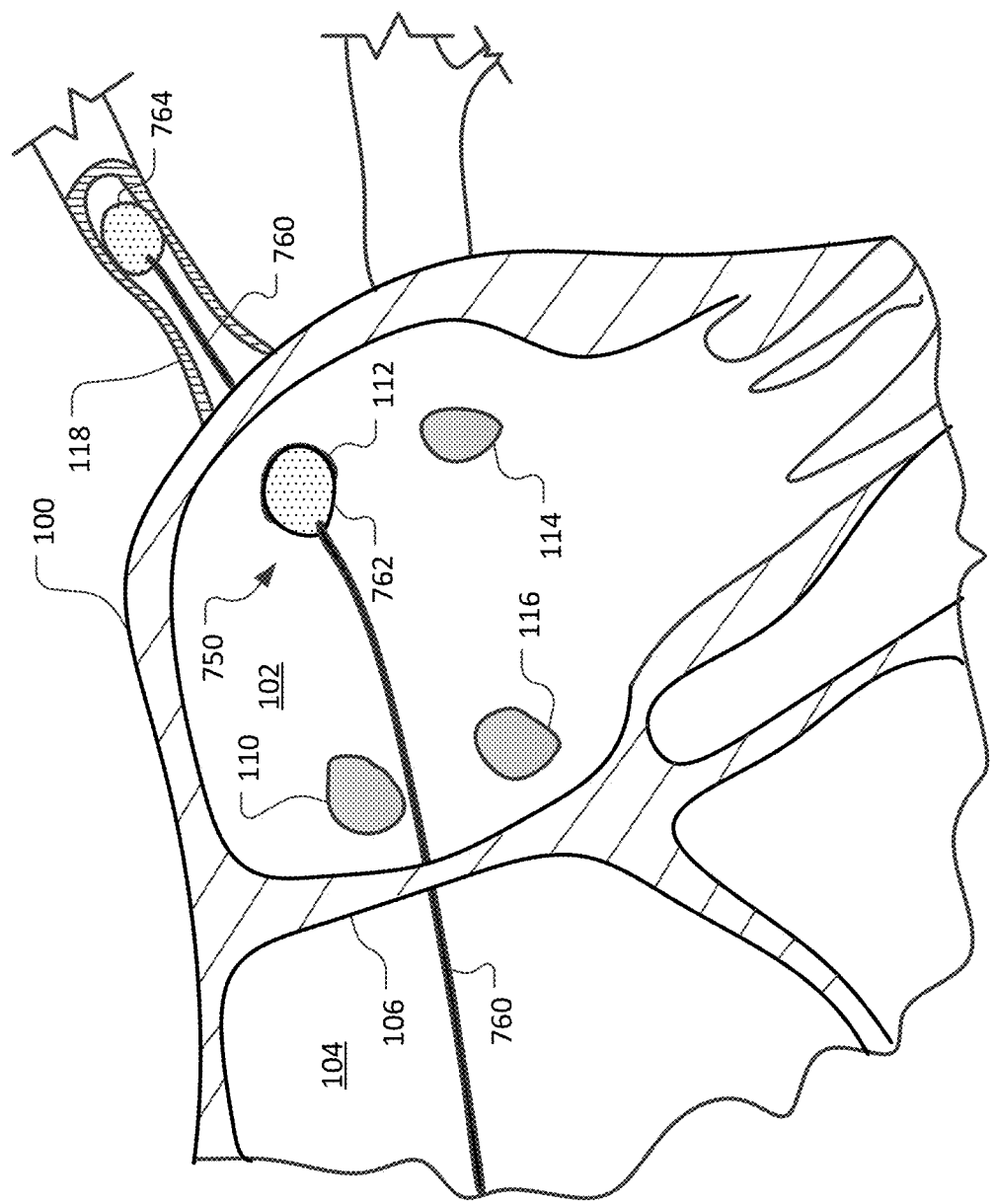
FIG. 8 is a schematic diagram of another catheter-based system for suctioning cells to cause cell death.

Referring to FIG. 8, another catheter-based system 750 can be used to apply suction to a vessel to cause death of cells of the vessel. Catheter based-system 750 includes a double balloon catheter 760. In some embodiments, a delivery sheath is included, in which double balloon catheter 760 is slidably disposed.

While the depicted implementation is described and illustrated as treating a pulmonary vein 118, it should be understood that the devices and techniques can be similarly applied in the context of other vessels such as, but not limited to, an aorta, a coronary artery, the superior vena cava, and the like.

Double balloon catheter 760 includes a proximal balloon 762 and a distal balloon 764. Distal balloon 764 is distally spaced apart from proximal balloon 762. Both balloons 762 and 764 are inflatable.

Proximal balloon 762 can be inflated to seal pulmonary vein 118 near its ostium 112. Distal balloon 764 can be inflated to seal pulmonary vein 118 at a location that is distal of the proximal balloon 762. Hence, with distal balloon 764 inflated at a distal location within pulmonary vein 118, and proximal balloon 762 inflated at a proximal location within pulmonary vein 118, a portion of pulmonary vein 118 (between the balloons 762 and 764) is fluidically isolated. Suction can then be applied via double balloon catheter 760. Such suction will cause a portion of pulmonary vein 118 between the balloons 762 and 764 to collapse to a smaller than natural diameter.

It has been found that by collapsing vessels to a smaller diameter using suction as described in the context of catheter-based system 750 cell death occurs. In other words, such a treatment provides a non-thermal method of causing cell death. Suctioning treatments porates the cell membranes and causes irreversible cell death. In some implementations, enough suction may be applied to completely collapse the vessel portion.

In some implementations, electroporation within the space between the balloons 762 and 764 is also optionally applied.

Figure 10:
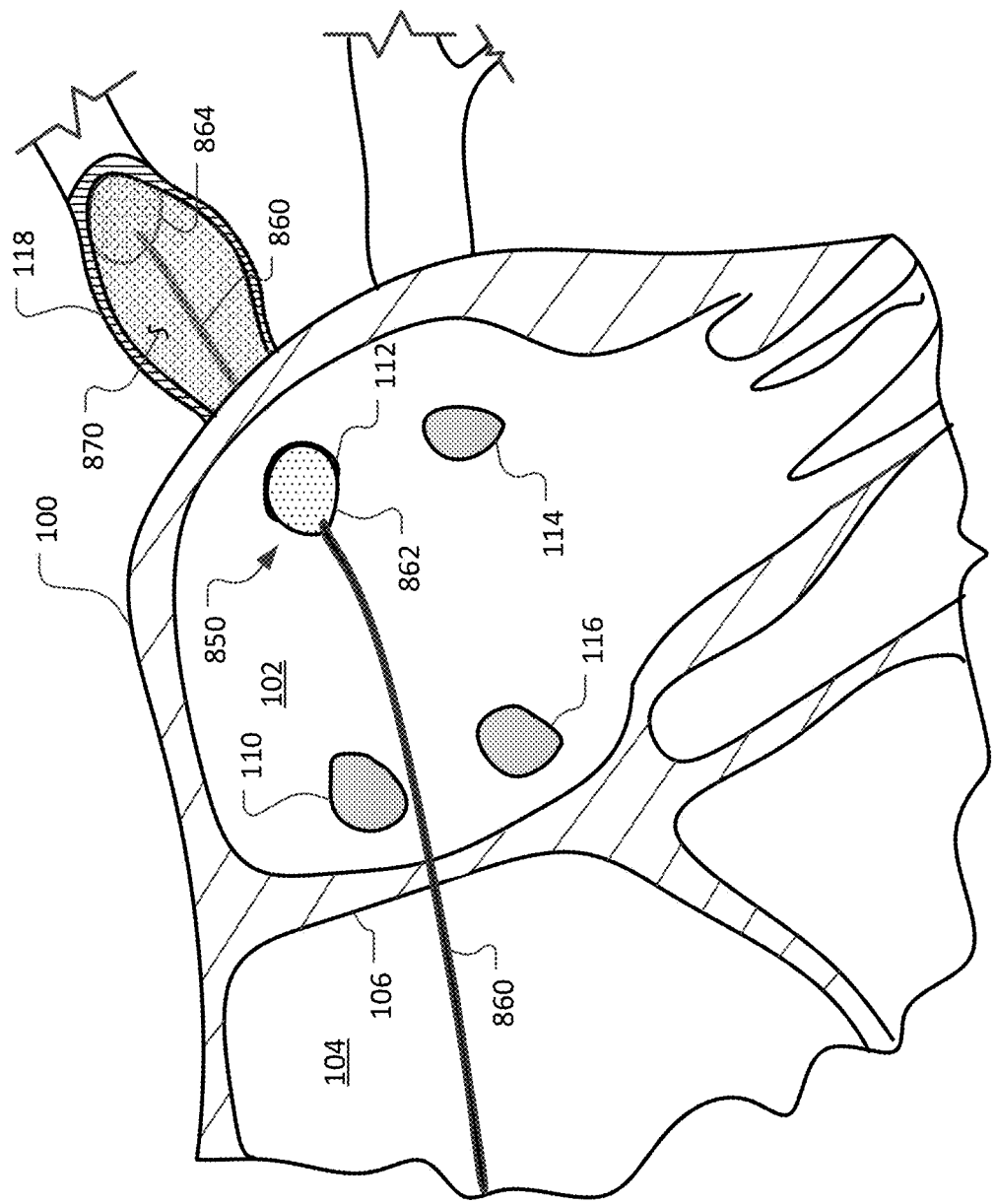
FIG. 10 is a schematic diagram of another catheter-based system for stretching cells to cause cell death.

In some implementations, the portion of pulmonary vein 118 (between the balloons 762 and 764) can be stretched (in addition to having the suction applied). For example, the embodiment described below in reference to FIG. 10 provides a technique for stretching the portion of pulmonary vein 118 between the balloons 762 and 764. In some implementations, a combination of stretching and suctioning can be applied to the same portion of pulmonary vein 118 using the same device. In some such implementations, a desired cyclic pattern of suction and stretch (and electroporation, in some implementations) can be applied to treat the portion of pulmonary vein 118 between the balloons 762 and 764. In some cases, such suction and/or stretching can be transduced so that the clinician can quantitatively perceive the safety and efficacy of the treatment being provided.

While, in some implementations, the suction/stretch destroys tissue, in some implementations the effects of the suction/stretch are reversible. In some such implementations, for example, the technique can be used for mapping for important tissue via alteration of tissue that is reversible (so there is no cell death). An example implementation of this technique would be around the AV node, etc. Also, sub-threshold stimulation can be applied/performed in some implementations.

Suction can also be used with any of the device/system embodiments provided herein to increase adherence of the tissue of interest for ablation to improve tissue/electrode contact. Alternatively, in some implementations suction can be used to adhere tissue of interest for ablation away from tissue of non-interest (e.g., to pull left atria tissue away from esophagus). Suction with irrigation (e.g., saline, 3% saline, ethanol, divalent cations, salt solutions, etc.), can be used in order to provide adjunct to cell membrane permeabilization. Suction can also be used for closure of iatrogenic septal defect/PFO by removal of the device and suctioning to apposing septal tissues closed after procedure.

Figure 9:
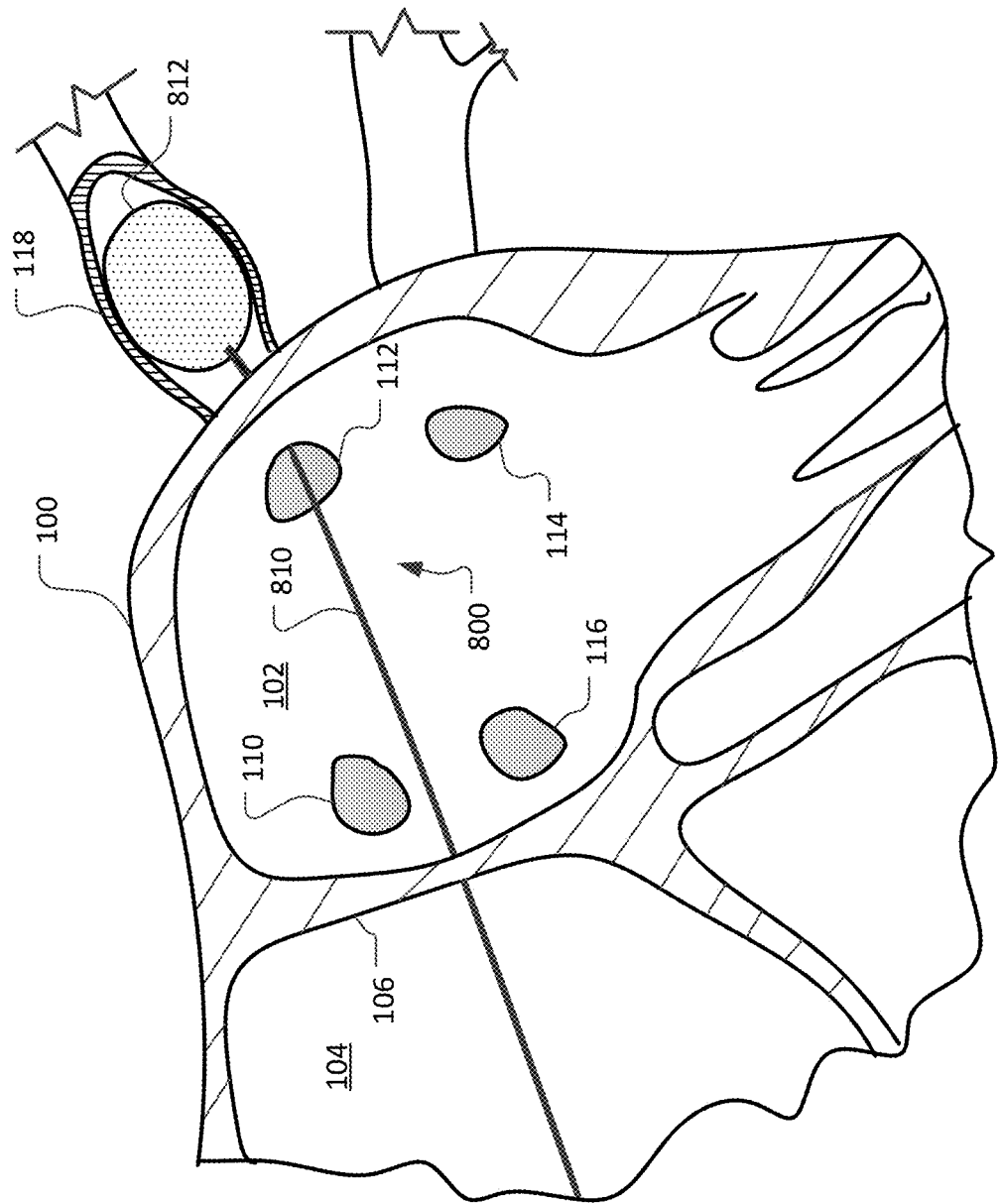
FIG. 9 is a schematic diagram of a catheter-based system for stretching cells to cause cell death.

Referring to FIG. 9, a catheter-based system 800 can be used to stretch a vessel to cause death of cells of the vessel. Catheter based-system 800 includes a balloon catheter 810 with a distal balloon 812. It should be understood that any of the balloon devices described herein can be implemented as distal balloon 812. In some embodiments, balloon catheter 810 is slidably disposed within a lumen of a delivery sheath (not shown).

While the depicted implementation is treating a pulmonary vein 118, it should be understood that the devices and techniques provided herein can be similarly applied in the context of other vessels such as, but not limited to, an aorta, a coronary artery, the superior vena cava, and the like; and to other tissue structures such as the atria, ventricles, epicardium, epicardial ganglia, and the like.

It has been found that, by expanding vessels to a larger than normal diameter (e.g., using an expansion device such as balloon catheter 810) cell death occurs. In other words, such a treatment provides a non-thermal method of causing cell death. Expansion treatments porates the cell membranes and causes irreversible cell death. In some implementations, enough stretch may be applied to enlarge the vessel up to (4) four times its normal diameter. In some implementations, enough stretch may be applied to enlarge the vessel up to 1.5 times, 2 times, 2.5 times, 3 times, 3.5 times, 4 times, or more than 4 times the normal diameter of the vessel.

The vessel stretching technique can be implement using any of the balloon devices described herein. In addition, the stretching technique can be implemented as an adjunct treatment with other treatment techniques described herein such as electroporation, suctioning of a vessel, delivery of an antimitotic pharmacological agent, and suctioning of particulate matter.

Referring to FIG. 10, another catheter-based system 850 can be used to stretch a vessel to cause death of cells of the vessel. Catheter based-system 850 includes a double balloon catheter 860 with a proximal balloon 862 and a distal balloon 864. Distal balloon 864 is distally spaced apart from proximal balloon 862. Both balloons 862 and 864 are inflatable. In some embodiments, double balloon catheter 860 is slidably disposed within a lumen of a delivery sheath (not shown).

While the depicted implementation is treating a pulmonary vein 118, it should be understood that the devices and techniques can be similarly applied in the context of other vessels such as, but not limited to, an aorta, a coronary artery, the superior vena cava, and the like.

Proximal balloon 862 can be inflated to seal pulmonary vein 118 near its ostium 112. Distal balloon 864 can be inflated to seal pulmonary vein 118 at a location that is distal of the proximal balloon 862. Hence, with distal balloon 864 inflated at a distal location within pulmonary vein 118, and proximal balloon 862 inflated at a proximal location within pulmonary vein 118, a portion of pulmonary vein 118 (between the balloons 862 and 864) is fluidically isolated. An inflation media 870 (e.g., saline) can then be supplied via double balloon catheter 860 to the fluidically isolated space between the balloons 862 and 864. The supply of the inflation media 870 can be delivered at a pressure that will cause pulmonary vein 118 to expand to a larger than natural diameter. In some embodiments, a pressure transducer can be included to monitor the pressure of the inflation media 870 for patient safety purposes. Such a pressure transducer can be located on or in one or more of catheter 860, proximal balloon 862, and distal balloon 864.

It has been found that, by expanding vessels to a larger than normal diameter using an expansion device such as balloon catheter 860, cell death occurs. In other words, such a treatment provides a non-thermal method of causing cell death. Expansion treatments porates the cell membranes and causes irreversible cell death. In some implementations, enough stretch may be applied to enlarge the vessel up to (4) four times its normal diameter. In some implementations, enough stretch may be applied to enlarge the vessel up to 1.5 times, 2 times, 2.5 times, 3 times, 3.5 times, 4 times, or more than 4 times the normal diameter of the vessel.

It can be observed that the design of catheter based-system 850 is generally analogous to the design of catheter-based system 750 (described above as used to administer suction within space in a vessel). Hence, a catheter-based system with two balloons is envisioned in the scope of this disclosure that can perform both suction (as described in the context of catheter-based system 750) and stretch (as described in the context of catheter-based system 850). That is, the same double-balloon design can be used to apply suction to cause a vessel to collapse to less than its normal diameter or pressure to cause the same vessel to expand to greater than its normal diameter. In some implementations, a repetitive series of applying suction, expansion, suction, expansion, and so on, can be performed to the same vessel using the double-balloon design described herein. In addition, the same double-balloon design could also be used to deliver electroporation (thermal methods of causing cell death) in some implementations.

It should also be understood, that the features and usage techniques described herein in relation to the various ablation devices can be combined with the features of other ablation device embodiments and usage techniques described herein. Accordingly, based on such combinations and sub-combinations, an extensive number of ablation device embodiments and usage techniques are envisioned and provided herein.

In addition to the implementations described above, additional treatment implementations are envisioned within the scope of this disclosure. For example, some additional important implementations, particularly for bipolar electroporation and for all drug-eluting or non-eluting electroporation balloon systems, is for treating malignancies, e.g., solid organ tumors could be electroporated in a bipolar fashion with balloons placed in two adjacent vessels or a vessel within the tumor along with adjacent vessels. In such an implementation, multiple balloons as well as virtual balloon-aided saline filled chambers and standalone electrodes may be used to treat the malignancy. The anode and cathodes may be varied with several balloons linked together as the anode and several others as the cathode and the other possible permutations when multiple balloons and electrodes are in play. In addition, an algorithm and software to cycle the anode and cathode (such as two balloons with anode and other eight as cathode, etc.), would be a part of the system. Such a system is envisioned to be a part of a closed-loop system with endpoints being electrograms in the case of cardiac or neural electroporation or hemolysis markers or apoptosis markers measured in real-time.

The hooded embodiments provided herein can have a number of hoods, e.g., one for capture/recirculation, as well as one for back-up/protection that can emit ultrasound, etc. to break up coagulum/ice balls as a safety back-up.

In another implementation, some of the device embodiments provided herein (e.g., the hood catheter systems) can be used to close/scar/fill in areas ("divots" or pockets) of tissue (e.g., in the atrium) so that pockets for emboli formation are not present.

In some embodiments, the devices and techniques provided herein can be used as a protective hood/suction circulation system in order to safely remove (alter while in place) the following+/−safely deliver of destructive drug or ablation or retrieval device for: tumors, vegetations, large thrombi, device removal-PFO, aortic/mitral/pulmonary/tricuspid valve, blood cysts, entrapped helical/circular catheters, biologic agents, anticancer agents, microbubbles, and/or antisense RNA.

The devices and techniques provided herein can also be extended to peripheral arterial and venous interventions. For example, in PAD balloons that are used for fem-pop lesions/interventions. In particular, for the use of electroporation to: drive anti-mitotic drugs into the tissues, or cholesterol"/plaque "proof" the lesions so that are no longer amenable to erosion/rupture.

In some embodiments, ablation (e.g., pulmonary vein ablation) can be performed by the devices and techniques provided herein and by additionally deploying one or more biodegradable scaffolds to prevent stenosis/collapse of the vessel structure.

The devices and techniques provided herein can also be extended to electroporation+/−DCB for ablation of the coronary sinus and its tributaries, and novel treatment for SCAD-electroporation to "proof" the intimal layer and DCB to prevent vessel stenosis. Further, in some embodiments DC energy can be used to tighten/sharpen/expand/polymerize balloon characteristics/shape/stiffness.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

It is very important to understand that one or more features from a particular device, system, or method described herein can be combined with one or more features from one or more other devices, systems, or methods described herein. Moreover, without limitation, all such combinations and permutations are within the scope of this disclosure.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for treating a tissue of a patient, said method comprising:
   inserting a catheter-based system into said patient, said system comprising:
   an ablation catheter device comprising an expandable member including one or more electrodes; and
   a catheter defining a lumen, the ablation catheter device being slidably disposed within the lumen, the catheter including an expandable distal end portion that has a conical or frustoconical shape when expanded;
   deploying said ablation catheter device near said tissue by inserting the expandable member into a vein or artery and then expanding the expandable member therein;
   expanding said expandable distal end portion into the conical or frustoconical shape;
   deploying said expanded expandable distal end portion by pressing the conical or frustoconical shape against a tissue wall surrounding an ostium of the vein or artery to enclose a space adjacent the ostium;
   supplying ablation energy from the one or more electrodes of the expandable member to the tissue; and
   suctioning said space via said catheter.

2. The method of claim 1, wherein the vein or artery is a pulmonary vein.

3. The method of claim 1, wherein the vein or artery is a renal artery.

4. The method of claim 1, further comprising, after said suctioning, irrigating said space with an irrigant supplied via said catheter.

5. The method of claim 4, further comprising, after said irrigating, suctioning said space via said catheter.

6. The method of claim 1, wherein the expandable member comprises a balloon member made of a porous or microporous material.

7. The method of claim 6, further comprising transmitting a liquid pharmacological agent through the porous or microporous material and to the tissue.

8. The method of claim 7, wherein the transmitting the liquid pharmacological agent to the tissue is performed simultaneously with the supplying the ablation energy to the tissue.

9. The method of claim 1, wherein the expandable member comprises one or more spikes or spindles on an outer surface of the expandable member.

10. The method of claim 9, wherein the expanding the expandable member results in the one or more spikes or spindles being positioned adjacent the tissue.

11. The method of claim 1, wherein the expandable member comprises a balloon member that comprises a bulbous proximal balloon portion and a generally cylindrical portion extending distally from the bulbous proximal balloon portion.

12. The method of claim 11, wherein the deploying said ablation catheter device comprises inserting the generally cylindrical portion into the vein or artery while the bulbous proximal balloon portion remains outside of the vein or artery.

13. The method of claim 1, wherein the expandable distal end portion comprises one or more return electrodes.

14. The method of claim 13, wherein the one or more return electrodes of the expandable distal end portion receive the ablation energy supplied from the one or more electrodes of the expandable member and passed through the tissue.

15. The method of claim 1, wherein the suctioning said space takes place during the supplying ablation energy and prior to contraction of the expandable member.

16. The method of claim 1, wherein the expandable distal end portion comprises ePTFE material.

17. The method of claim 16, wherein the expandable distal end portion comprises a framework or mesh of Nitinol material.

18. The method of claim 16, wherein the expandable distal end portion acts as a filter device to provide embolic protection.

\* \* \* \* \*